(12) United States Patent
Esser et al.

(10) Patent No.: US 12,264,194 B2
(45) Date of Patent: Apr. 1, 2025

(54) **DECREASING *STAPHYLOCOCCUS AUREUS* INFECTIONS IN COLONIZED PATIENTS**

(71) Applicant: MedImmune, LLC, Gaithersburg, MD (US)

(72) Inventors: Mark Esser, Gaithersburg, MD (US); Alexey Ruzin, Gaithersburg, MD (US); Hasan Jafri, Gaithersburg, MD (US); Kathryn Shoemaker, Gaithersburg, MD (US); Bret Sellman, Gaithersburg, MD (US); Li Yu, Gaithersburg, MD (US)

(73) Assignee: MedImmune, LLC, Gaithersburg, MD (US)

( * ) Notice: Subject to any disclaimer, the term of this patent is extended or adjusted under 35 U.S.C. 154(b) by 727 days.

(21) Appl. No.: 17/438,828

(22) PCT Filed: Mar. 12, 2020

(86) PCT No.: PCT/US2020/022226
§ 371 (c)(1),
(2) Date: Sep. 13, 2021

(87) PCT Pub. No.: WO2020/185986
PCT Pub. Date: Sep. 17, 2020

(65) Prior Publication Data
US 2022/0127338 A1    Apr. 28, 2022

Related U.S. Application Data

(60) Provisional application No. 62/817,934, filed on Mar. 13, 2019.

(51) Int. Cl.
| C07K 16/12 | (2006.01) |
| C12Q 1/686 | (2018.01) |
| C12Q 1/689 | (2018.01) |
| A61K 39/00 | (2006.01) |

(52) U.S. Cl.
CPC .......... C07K 16/1271 (2013.01); C12Q 1/686 (2013.01); C12Q 1/689 (2013.01); *A61K 2039/505* (2013.01); *A61K 2039/545* (2013.01); *C07K 2317/52* (2013.01); *C12Q 2600/106* (2013.01)

(58) Field of Classification Search
None
See application file for complete search history.

(56) References Cited

U.S. PATENT DOCUMENTS

| 9,527,905 | B2 | 12/2016 | Sellman et al. |
| 9,845,348 | B2 | 12/2017 | Sellman et al. |
| 9,879,070 | B2 | 1/2018 | Sellman et al. |
| 10,457,724 | B2 | 10/2019 | Sellman et al. |
| 10,730,934 | B2 | 8/2020 | Sellman et al. |
| 10,759,849 | B2 | 9/2020 | Sellman et al. |
| 11,059,884 | B2 | 7/2021 | Tkaczyk et al. |
| 11,168,132 | B2 | 11/2021 | Sellman et al. |
| 11,168,133 | B2 | 11/2021 | Tkaczyk et al. |
| 11,447,543 | B2 | 9/2022 | Sellman et al. |
| 11,578,119 | B2 | 2/2023 | Tkaczyk et al. |
| 2011/0165172 | A1 | 7/2011 | Yarranton et al. |
| 2019/0077851 | A1 | 3/2019 | Jafri et al. |
| 2022/0089699 | A1 | 3/2022 | Tkaczyk et al. |

FOREIGN PATENT DOCUMENTS

| CN | 103443285 A | 12/2013 |
| WO | WO-2012109285 A2 | 8/2012 |
| WO | WO-2013093693 A1 | 6/2013 |
| WO | WO-2014074540 A2 | 5/2014 |
| WO | WO-2015196011 A1 | 12/2015 |
| WO | WO-2017075188 A2 | 5/2017 |
| WO | WO-2020076789 A2 | 4/2020 |
| WO | WO-2020185986 A1 | 9/2020 |

OTHER PUBLICATIONS

Coppens, J., et al., "Comparison of GeneXpert MRSA/SA ETA assay with semi-quantitative and quantitative cultures and nuc gene-based qPCR for detection of *Staphylococcus aureus* in endotracheal aspirate samples," Antimicrob Resist. Infect. Control 8(4):1-7, BMC, United Kingdom (Jan. 2019).
Co-Pending U.S. Appl. No. 17/152,725, inventors Jafri, H., et al., filed Jan. 19, 2021 (Not Published).
Esperatti, M., et al., "Nosocomial Pneumonia in the Intensive Care Unit Acquired by Mechanically Ventilated versus Nonventilated Patients," Am. J. Resp. Crit. Care Med. 182(12):1533-1539, American Thoracic Society, United States (2010).
Foletti, D., et al., "Mechanism of action and in vivo efficacy of a human-derived antibody against *Staphylococcus aureus* α-hemolysin," J. Mol. Biol. 425(10):1641-1654, Elsevier, Netherlands (2013).
Francois, B., et al., "Safety and tolerability of a single administration of AR-301, a human monoclonal antibody, in ICU patients with severe pneumonia caused by *Staphylococcus aureus*: first-in-human trial," Intensive Care Medicine 44(11):1787-1796, SpringerLink, United States (2018).
Hazenbos, W.L., et al., "Novel staphylococcal glycosyltransferases SdgA and SdgB mediate immunogenicity and protection of virulence-associated cell wall proteins," PLOS Pathog. 9(10):e1003653, PLOS, United States (2013).
Hua, L., et al., "Assessment of an anti-alpha-toxin monoclonal antibody for prevention and treatment of *Staphylococcus aureus*-induced pneumonia," Antimicrob. Agents Chemother. 58(2):1108-1117, American Society for Microbiology, United States (2014).
Hua, L., et al., "MEDI4893* Promotes Survival and Extends the Antibiotic Treatment Window in a *Staphylococcus aureus* Immunocompromised Pneumonia Model," Antimicrob. Agents and Chemotherapy 59(8):4526-4532, American Society for Microbiology, United States (2015).

(Continued)

*Primary Examiner* — Jennifer E Graser
(74) *Attorney, Agent, or Firm* — Sterne, Kessler, Goldstein & Fox P.L.L.C.

(57) ABSTRACT

The present disclosure is directed to methods of treating subjects colonized with *S aureus* with an anti-alpha toxin antibody or antigen-binding fragment thereof. The methods can decrease the incidence of infection attendant to the presence of *S. aureus* in the subject.

20 Claims, 12 Drawing Sheets
Specification includes a Sequence Listing.

(56) References Cited

OTHER PUBLICATIONS

Karauzum, H., et al., "Synthetic human monoclonal antibodies toward staphylococcal enterotoxin B (Seb) protective against toxic shock syndrome," J. Biol. Chem. 287(30):25203-25215, Elsevier, Netherlands (2012).

Lowy, F.D., "*Staphylococcus aureus* infections," N. Engl. J. Med. 339(8):520-532, Massachusetts Medical Society, United States (1998).

Mashburn, L.M., et al., "*Staphylococcus aureus* serves as an iron source for Pseudomonas aeruginosa during in vivo coculture," J. Bacteriol. 187(2):554-566, American Society for Microbiology, United States (2005).

Rouha, H., et al., "Five birds, one stone: neutralization of a-hemolysin and 4 bi-component leukocidins of *Staphylococcus aureus* with a single human monoclonal antibody," MAbs. 7(1):243-254, Taylor & Francis, United Kingdom (2015).

Ruzin, A., et al., "2160: Performance of the Cepheid Rapid PCR Test for Patient Screening and Association with Efficacy of Suvratoxumab, A Novel Anti-*Staphylococcus aureus* Monoclonal Antibody, During the Phase 2 SAATELLITE study," Open Forum Infectious Diseases 6(Supplement 2):S733, Infectious Disease Society of America, United States (Oct. 2019).

Spellberg, B., and Talbot, G., "Recommended Design Features of Future Clinical Trials of Antibacterial Agents for Hospital-Acquired Bacterial Pneumonia and Ventilator-Associated Bacterial Pneumonia," Clinical Infectious Diseases 51(Supplement_1):S150-S170, Oxford Academic Press, United Kingdom (2010).

Wilke, G.A., and Wardenburg, J.B., "Role of a disintegrin and metalloprotease 10 in *Staphylococcus aureus* α-hemolysin-mediated cellular injury," Proc. Natl. Acad. Sci. USA 107(30):13473-13478, National Academy of Sciences, United States (2010).

Adhikari, R.P., et al., "Novel structurally designed vaccine for *S. aureus* α-hemolysin: protection against bacteremia and pneumonia," PLoS One 7:e38567, pp. 1-11, Public Library of Science, United States (Jun. 2012).

Becker, R.E.N., et al., "Tissue-Specific Patterning of Host Innate Immune Responses by *Staphylococcus aureus* α-Toxin," J Innate Immun., 6:619-631, SAGE, United States (May 2014).

Bhakdi, S.J., and Tranum-Jensen, J., "Alpha-toxin of *Staphylococcus aureus*," Microbiol. Rev., 55(4):733-751, American Society for Microbiology, United States (Dec. 1991).

Wardenburg, J.B., and Schneewind, O., "Vaccine protection against *Staphylococcus aureus* pneumonia," J. Exp. Med., 205:287-294, Rockefeller University Press, United States (Feb. 2008).

Inoshima, N., et al., "Genetic requirement for ADAM10 in severe *Staphylococcus aureus* skin infection," J. Invest. Dermatol., 132(5):1513-1516, Elsevier, Netherlands (Mar. 2012).

Oganesyan, V., et al., "Mechanisms of Neutralization of a Human Anti-α-toxin Antibody," J. Biol. Chem., 289(43):29874-29880, American Society for Biochemistry and Molecular Biology, United States (Oct. 2014).

Powers, M.E., et al., "Synergistic Action of *Staphylococcus aureus* α-Toxin on Platelets and Myeloid Lineage Cells Contributes to Lethal Sepsis," Cell Host Microbe, 17(6): 775-787, Cell Press, United States (Jun. 2015).

Powers, M.E., et al., "ADAM10 mediates vascular injury induced by *Staphylococcus aureus* α-hemolysin," J Infect. Dis., 206(3):352-356, Oxford Academic, United Kingdom (Apr. 2012).

Ragle, B.E., et al., "Anti-Alpha-Hemolysin Monoclonal Antibodies Mediate Protection against *Staphylococcus aureus* Pneumonia," Infect. Immun., 77(7): 2712-2718, American Society for Microbiology, United States (Apr. 2009).

Tkaczyk, C., et al., "Identification of Anti-Alpha Toxin Monoclonal Antibodies That Reduce the Severity of *Staphylococcus aureus* Dermonecrosis and Exhibit a Correlation Between Affinity and Potency," Clinical and Vaccine Immunology 19(3):377-385, American Society for Microbiology, United States (Mar. 2012).

Yu, X-Q., et al., "Safety, Tolerability, and Pharmacokinetics of MEDI4893, an Investigational, Extended-Half-Life, Anti-*Staphylococcus aureus* Alpha-Toxin Human Monoclonal Antibody, in Healthy Adults," Antimicrob Agents Chemother 61(1):e01020-16, pp. 1-9, American Society for Microbiology, United States (Oct. 2016).

International Search Report and Written Opinion mailed Jun. 15, 2020, in International Application No. PCT/US2020/022226, European Patent Office, Netherlands, 14 pages.

English language translation of Office Action for Chinese Patent Application No. 202080034698.2, dated Sep. 7, 2024, 3 pages.

DECREASING *STAPHYLOCOCCUS AUREUS* INFECTIONS IN COLONIZED PATIENTS

CROSS-REFERENCE TO RELATED APPLICATIONS

This application is the United States National Phase of International Application No. PCT/US2020/022226, filed on Mar. 12, 2020, which claims the benefit of U.S. Provisional Patent Application No. 62/817,934, filed on Mar. 13, 2019, each of which is incorporated herein by reference in its entirety.

REFERENCE TO SEQUENCE LISTING SUBMITTED ELECTRONICALLY

The content of the electronically submitted sequence listing (Name: 2943_1180001_Seqlisting_ST25; Size: 18.4 KB (18,845 bytes); and Date of Creation: Sep. 13, 2021) is herein incorporated by reference in its entirety.

BACKGROUND

Bacterial pneumonia occurring within the hospitalized or intensive care unit (ICU) population is a clinically significant and serious disease that contributes significantly to morbidity and mortality. This constitutes the second leading type of nosocomial infection and the leading cause of death from nosocomial infection in the United States (Spellberg and Talbot, 2010). *aureus* is the primary cause of nosocomial pneumonia. A recent study of European ICUs reported that 23% of mechanically ventilated ICU patients developed pneumonia caused by *S. aureus*, with over half caused by methicillin-resistant *Staphylococcus aureus* (MRSA) (Esperatti et al, 2010).

*Staphylococcus aureus* also causes a wide array of additional of diseases including skin and soft tissue infections, endocarditis, osteomyelitis, pneumonia, and bacteremia (Lowy, F. D., N. *Engl. J. Med.*, 339(8): 520-32 (1998)). During infection, *S. aureus* releases a number of toxins, with alpha toxin (AT) as the most prevalent virulence factor causing tissue invasion and necrosis (Wilke and Bubeck Wardenburg, 2010). The pivotal role of AT in *S. aureus* pathogenesis is supported by animal models (dermonecrosis, pneumonia, sepsis, endocarditis, and mastitis) and by observational studies in humans in which the presence of anti-AT antibodies during severe infections was associated with improved outcome.

Preclinical studies indicate monoclonal antibody-based approaches hold promise for prophylaxis and adjunctive therapy against *S. aureus* infections (see, e.g., Hazenbos et al., *PLoS Pathog.*, 9(10):e1003653. doi: 10.1371/journal.ppat.10036532013 (2013); Rouha, H., *MAbs*, 7(1): 243-254 (2015); Foletti et al., *J. Mol. Biol.*, 425(10): 1641-1654 (2013); Karauzum et al., *J Biol Chem.*, 287(30): 25203-15 (2012); and Hua et al., *Antimicrob Agents Chemother.*, 58(2): 1108-17 (2014)). Anti-AT antibodies show promising results in their ability to treat and prevent *S. aureus* infections. MEDI4893, or suvratoxumab, is a human monoclonal antibody with an extended half-life that binds AT with high affinity and effectively blocks AT pore formation in target cell membranes. Preclinical results have demonstrated that prophylaxis with an anti-AT antibody comprising the MEDI4893 binding region reduced disease severity in dermonecrosis, pneumonia and lethal bacteremia/sepsis murine infection models (see e.g., WO 2012/109285 and WO 2014/074540, each of which is herein incorporated by reference in its entirety).

However, *S. aureus* infections such as pneumonia can develop very quickly in patients colonized with *S. aureus*, so methods of identifying at-risk patients who will achieve maximum benefit from anti-AT antibodies are needed.

BRIEF SUMMARY OF THE INVENTION

*Staphylococcus aureus* (*S. aureus*) pneumonia is a life-threatening complication that occurs early in intensive care unit (ICU) patients on mechanical ventilation in spite of infection control and antibiotics. As demonstrated here, anti-alpha toxin (AT) antibodies were evaluated for the prevention of *S. aureus* pneumonia and where shown to be associated with clinically meaningful efficacy (≥25% relative risk reduction) and acceptable safety. In particular, a 32% reduction in *S. aureus* pneumonia was observed in patients receiving anti-AT antibodies and there were no safety concerns. In addition, even greater efficacy was observed in certain subsets of patients. Accordingly, methods of identifying patients at risk of developing *S. aureus* infections who will benefit from receiving an anti-AT antibody are provided herein.

Provided herein are methods of treating a subject colonized with *Staphylococcus aureus* (*S. aureus*) comprising administering an antibody or antigen-binding fragment thereof that binds to *S. aureus* alpha toxin (AT) to the subject, wherein polymerase chain reaction (PCR) has been used to detect the level of *S. aureus* in a sample obtained from the subject. In certain instances, the sample obtained from the subject has a level of *S. aureus* that does not exceed a level of *S. aureus* that correlates to a polymerase chain reaction (PCR) cycle threshold (Ct) value. In certain instances, the method decreases the incidence of infection attendant to the presence of *S. aureus* in the subject.

Provided herein are methods of preventing a *S. aureus* infection in a subject comprising administering an antibody or antigen-binding fragment thereof that binds to *S. aureus* AT to the subject, wherein a sample obtained from the subject has a level of *S. aureus* that does not exceed a level of *S. aureus* that correlates to a PCR Ct value.

Provided herein are methods for reducing the incidence of *S. aureus* pneumonia in a subject comprising administering to the subject suvratoxumab, wherein the reduction is determined by clinical, microbiological, and radiographic measures, optionally wherein the incidence is reduced by about 30%.

Provided herein are methods for reducing the incidence of all-cause pneumonia in a subject comprising administering to the subject suvratoxumab, wherein the reduction is determined by clinical, microbiological, and radiographic measures, optionally wherein the incidence is reduced by about 30%.

In certain instances, the infection is determined by clinical, microbiological, and radiographic measures.

In certain instances, the clinical measures comprises abnormal temperature, abnormal white blood cell count, cough, purulent sputum, bronchial breath sounds, dyspnea, tachypnea (respiratory rate>30 breaths/minute), hypoxemia, or any combination thereof.

In certain instances, the microbiological measure comprises a respiratory specimen, blood culture, pleural fluid aspirate, or lung tissue culture positive for *S. aureus*.

In certain instances, the radiographic measure comprises new or worsening infiltrate on a chest X-ray.

In certain instances, PCR has been used to detect the level of *S. aureus* in a sample obtained from the subject. In certain instances, the sample obtained from the subject has a level of *S. aureus* that does not exceed a level of *S. aureus* that correlates to a polymerase chain reaction (PCR) cycle threshold (Ct) value.

In certain instances, the methods provided herein further comprise detecting a level of *S. aureus* in a sample obtained from the subject.

In certain instances, the sample obtained from the subject has a level of *S. aureus* that does not exceed a level of *S. aureus* that correlates to the PCR Ct value of 29 or above. In certain instances, the PCR Ct value of 29 corresponds to a concentration of about 1600 to about 1700 colony forming units (CFU)/ml of *S. aureus*.

Provided herein are methods of treating a subject colonized with *S. aureus* infection comprising administering an antibody or antigen-binding fragment thereof that binds to *S. aureus* AT to the subject, wherein a sample obtained from the subject has a concentration of *S. aureus* that does not exceed 1700 CFU/ml. In certain instances, the method decreases the incidence of infection attendant to the presence of *S. aureus* in the subject.

Provided herein are methods of preventing a *S. aureus* infection in a subject comprising administering an antibody or antigen-binding fragment thereof that binds to *S. aureus* AT to the subject, wherein a sample obtained from the subject has a concentration of *S. aureus* that does not exceed 1700 CFU/ml.

In certain instances, the concentration of *S. aureus* AT was measured using PCR.

In certain instances, the subject is colonized with *S. aureus*.

In certain instances, a sample obtained from the subject has at least a level of *S. aureus* that correlates to a PCR Ct value. In certain instances, a sample obtained from the subject has at least a level of *S. aureus* that correlates to a PCR Ct value of 3.

In certain instances, the level of *S. aureus* is detected in no more than 3 hours, optionally no more than 2 hours.

In certain instances, the PCR detects *S. aureus* protein A.

In certain instances, the subject is ventilated, optionally wherein the subject is mechanically ventilated. In certain instances, the subject is taking antibiotics.

In certain instances, the sample is a skin or soft tissue sample. In certain instances, the sample is obtained from the lower respiratory tract of the subject. In certain instances, the sample is an endotracheal aspirate. In certain instances, the sample is a tracheal sample. In certain instances, the sample is a bronchial sample.

In certain instances, the sample contains bacteria that would not grow in a culture to identify *S. aureus*. In certain instances, the sample contains bacteria that are not *Staphylococcus*. In certain instances, the *S. aureus* is antibiotic-resistant. In certain instances, the methods provided herein further comprise determining whether the *S. aureus* is antibiotic resistant.

In certain instances, the *S. aureus* is methicillin-resistant. In certain instances, the methods provided herein further comprise determining whether the *S. aureus* is methicillin-resistant.

In certain instances, the resistance is determined using PCR.

In certain instances, the infection is pneumonia. In certain instances, the infection is intensive care unit (ICU) pneumonia.

In certain instances, the subject is human.

In certain instances, the antibody or antigen-binding fragment thereof that binds to *S. aureus* AT binds to the same *S. aureus* AT epitope as an antibody comprising a VH comprising the amino acid sequence of SEQ ID NO:7 and a VL comprising the amino acid sequence of SEQ ID NO:8. In certain instances, the antibody or antigen-binding fragment thereof that binds to *S. aureus* AT competitively inhibits binding of an antibody comprising a VH comprising the amino acid sequence of SEQ ID NO:7 and a VL comprising the amino acid sequence of SEQ ID NO:8 to *S. aureus* AT.

In certain instances, the antibody or antigen-binding fragment thereof that binds to *S. aureus* AT comprises the VH CDR1, VH CDR2, VH CDR3, VL CDR1, VL CDR2, and VL CDR3 of MEDI4893. In certain instances, the antibody or antigen-binding fragment thereof that binds to *S. aureus* AT comprises a variable heavy chain (VH) complementarity determining region (CDR) 1 comprising the amino acid sequence of SEQ ID NO:1, a VH CDR2 comprising the amino acid sequence of SEQ ID NO:2, a VH CDR3 comprising the amino acid sequence of SEQ ID NO:3, a variable light chain (VL) CDR1 comprising the amino acid sequence of SEQ ID NO:4, a VL CDR2 comprising the amino acid sequence of SEQ ID NO:5, and a VL CDR3 comprising the amino acid sequence of SEQ ID NO:6.

In certain instances, the antibody or antigen-binding fragment thereof that binds to *S. aureus* AT comprises a VH comprising the amino acid sequence of SEQ ID NO:7. In certain instances, the antibody or antigen-binding fragment thereof that binds to *S. aureus* AT comprises a VL comprising the amino acid sequence of SEQ ID NO:8.

In certain instances, the antibody or antigen-binding fragment thereof that binds to *S. aureus* AT comprises a heavy chain comprising the amino acid sequence of SEQ ID NO:9. In certain instances, the antibody or antigen-binding fragment thereof that binds to *S. aureus* AT comprises a light chain comprising the amino acid sequence of SEQ ID NO:10.

In certain instances, the antibody or antigen-binding fragment that binds to *S. aureus* AT further comprises a heavy chain constant region. In certain instances, the heavy chain constant region is selected from the group consisting of human immunoglobulin $IgG_1$, $IgG_2$, $IgG_3$, $IgG_4$, $IgA_1$, and $IgA_2$ heavy chain constant regions. In certain instances, the heavy chain constant region is a human $IgG_1$ constant region.

In certain instances, the antibody or antigen-binding fragment that binds to *S. aureus* AT further comprises a light chain constant region. In certain instances, the light chain constant region is selected from the group consisting of human immunoglobulin IgGκ and IgGλ light chain constant regions. In certain instances, the light chain constant region is a human IgGκ light chain constant region.

In certain instances, the antibody or antigen-binding fragment thereof that binds to *S. aureus* AT is an IgG antibody or antigen-binding fragment thereof.

In certain instances, the antibody or antigen-binding fragment thereof that binds to *S. aureus* AT comprises an Fc region that has been engineered to improve half-life. In certain instances, the antibody or antigen-binding fragment thereof that binds to *S. aureus* AT comprises an Fc region with a YTE mutation.

In certain instances, the antibody or antigen-binding fragment that binds to *S. aureus* AT is a monoclonal antibody or antigen-binding fragment.

In certain instances, the antibody or antigen-binding fragment that binds to *S. aureus* AT is a full-length antibody. In certain instances, the antibody or antigen-binding fragment that binds to S. aureus AT is an antigen-binding fragment. In certain instances, the antigen-binding fragment comprises a Fab, Fab', F(ab')$_2$, single chain Fv (scFv), disulfide linked Fv, intrabody, IgGΔCH2, minibody, F(ab')$_3$, tetrabody, triabody, diabody, DVD-Ig, Fcab, mAb$^2$, (scFv)$_2$, or scFv-Fc.

In certain instances, the antibody or antigen-binding fragment thereof that binds to S. aureus AT has an affinity of 80-100 pM for S. aureus AT.

In certain instances, the antibody or antigen-binding fragment thereof is suvratoxumab.

In certain instances, 2000 mg of the antibody or antigen-binding fragment is administered. In certain instances, 5000 mg of the antibody or antigen-binding fragment is administered.

In certain instances, the preventing an S. aureus infection comprises toxin neutralization, inducing opsonophagocytosis, inhibiting thromboembolic lesion formation, inhibiting S. aureus-associated sepsis, or any combination of the foregoing.

Provided herein are antibodies or antigen-binding fragments thereof that bind to S. aureus AT for use in treating a subject colonized with Staphylococcus aureus (S. aureus), wherein a sample obtained from the subject has a level of S. aureus that does not exceed a level of S. aureus that correlates to a polymerase chain reaction (PCR) cycle threshold (Ct) value. In certain instances, the treating decreases the incidence of infection attendant to the presence of S. aureus in the subject.

Provided herein are antibodies or antigen-binding fragments thereof that bind to S. aureus AT for use in prevention of S. aureus infection in a subject colonized with S. aureus, wherein a sample obtained from the subject has a level of S. aureus that does not exceed a level of S. aureus that correlates to a PCR Ct value.

In certain instances, the sample obtained from the subject has a level of S. aureus that does not exceed a level of S. aureus that correlates to the PCR Ct value of 29. In certain instances, the antibody or antigen-binding fragment thereof is not administered to the subject in case S. aureus levels that do exceed the level of S. aureus that correlates to a PCR Ct value are detected in a sample obtained from the subject.

Provided herein are in vitro methods of identifying a subject colonized with S. aureus to be responsive to an antibody or antigen-binding fragment thereof that binds to S. aureus AT comprising detecting S. aureus levels in a sample obtained from the subject, wherein a level of S. aureus that does not exceed a level of S. aureus that correlates to a PCR Ct value is indicative that the subject is responsive to the antibody or antigen-binding fragment thereof. In certain instances, the PCR Ct value is 29.

DETAILED DESCRIPTION OF THE INVENTION

Figure 1:
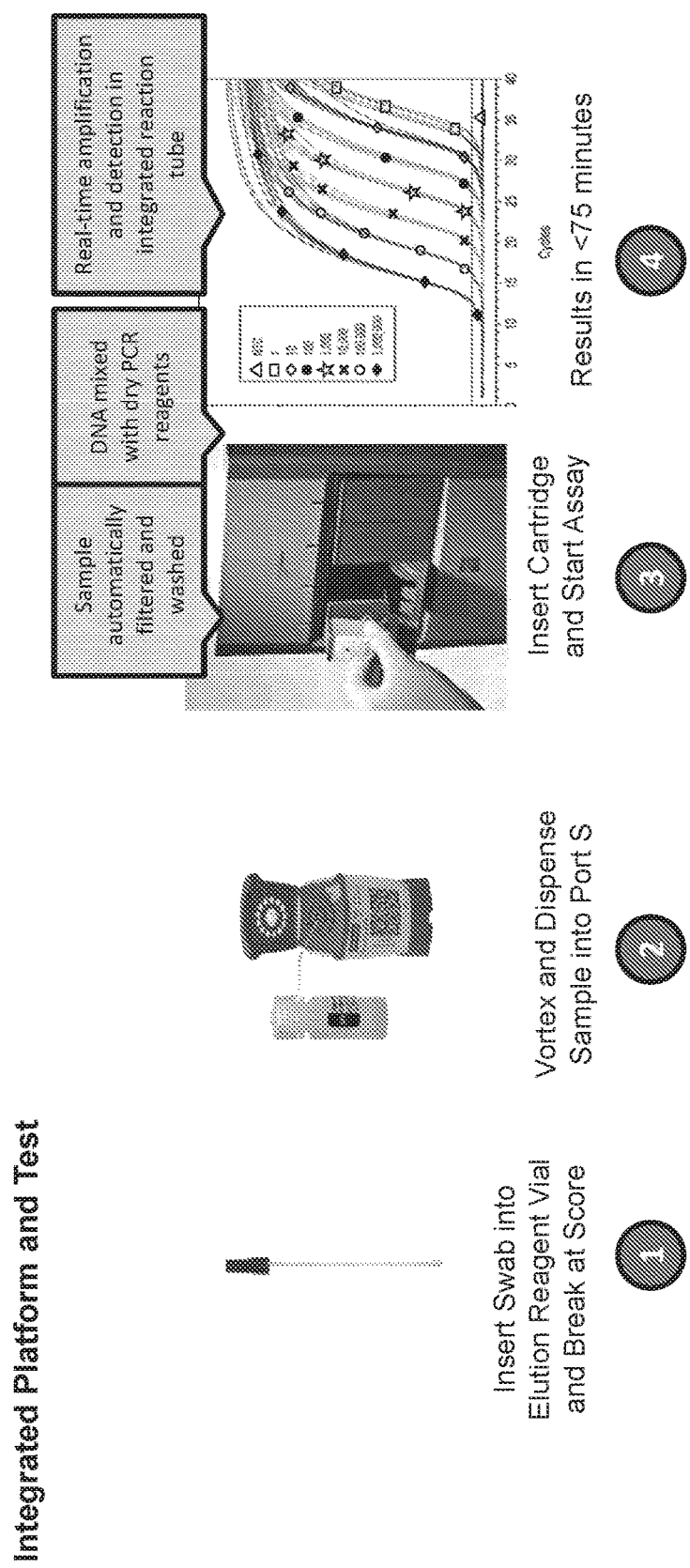
FIG. 1 is a schematic illustrating the use of an S. aureus PCR test for rapid patient identification. The PCR test produces a cycle threshold (Ct) value that represents the number of PCR cycles needed to reach a threshold signal (represented by the horizontal line in the graph on the right side of the Figure). The Ct value is inversely related to the bacterial load: a higher number of S. aureus in a sample requires fewer cycles to reach the threshold level and therefore has a low Ct value (curves on the left side of the graph), whereas a lower number of S. aureus in a sample requires more cycles to reach the threshold level and therefore has a higher Ct value (curves on the right side of the graph). (See Example 1.)

The present disclosure is directed to methods of preventing *S. aureus* infections in patients with low levels of *S. aureus* colonization and methods of identifying patients who are colonized with *S. aureus* and who will benefit from an alpha-toxin antibody.

I. Definitions

The use of the terms "a" and "an" and "the" and "at least one" and similar referents in the context of describing the invention (especially in the context of the following claims) are to be construed to cover both the singular and the plural, unless otherwise indicated herein or clearly contradicted by context.

The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context.

The terms "comprising," "having," "including," and "containing" are to be construed as open-ended terms (i.e., meaning "including, but not limited to,") unless otherwise noted.

As used herein, the term "alpha toxin" or "AT" refers to bacterial alpha toxin polypeptides including, but not limited to, native alpha toxin polypeptides and isoforms of alpha toxin polypeptides. "Alpha toxin" encompasses full-length, unprocessed alpha toxin polypeptides as well as forms of alpha toxin polypeptides that result from processing within the cell. As used herein, the term "*S. aureus* alpha toxin" refers to a polypeptide comprising the amino acid sequence of

```
                                     (SEQ ID NO: 12)
adsdiniktgttdigsnttvktgdlvtydkengmhkkvfysfiddknhnk kllvirtkgtiagqyrvyseeganksglawpsafkvqlqlpdnevaqisd yyprnsidtkeymsfitygfngnvtgddtgkiggliganvsightlkyvq pdfktilesptdkkvgwkvifnnmvnqnwgpydrdswnpvygnqlfmktr ngsmkaadnfldpnkassllssgfspdfatvitmdrkaskqqtnidviye rvrddyqlhwtstnwkgtntkdkwtdrsserykidwekeemtn.
```

The *S. aureus* alpha toxin H35L mutant has the sequence

```
                                     (SEQ ID NO: 13)
adsdiniktgttdigsnttvktgdlvtydkengmlkkvfysfiddknhnk kllvirtkgtiagqyrvyseeganksglawpsafkvqlqlpdnevaqisd yyprnsidtkeymstltygfngnvtgddtgkiggliganvsightlkyvq pdfktilesptdkkvgwkvifnnmvnqnwgpydrdswnpvygnqlfmktm gsmkaadnfldpnkassllssgfspdfatvitmdrkaskqqtnidviyer vrddyqlhwtstnwkgtntkdkwtdrsserykidwekeemtn.
```

An "alpha toxin polynucleotide," "alpha toxin nucleotide," or "alpha toxin nucleic acid" refer to a polynucleotide encoding alpha toxin.

The term "antibody" means an immunoglobulin molecule that recognizes and specifically binds to a target, such as a protein, polypeptide, peptide, carbohydrate, polynucleotide, lipid, or combinations of the foregoing through at least one antigen recognition site within the variable region of the immunoglobulin molecule. As used herein, the term "antibody" encompasses intact polyclonal antibodies, intact monoclonal antibodies, chimeric antibodies, humanized antibodies, human antibodies, fusion proteins comprising an antibody, and any other modified immunoglobulin molecule so long as the antibodies exhibit the desired biological activity. An antibody can be of any the five major classes of immunoglobulins: IgA, IgD, IgE, IgG, and IgM, or subclasses (isotypes) thereof (e.g. IgG1, IgG2, IgG3, IgG4, IgA1 and IgA2), based on the identity of their heavy-chain constant domains referred to as alpha, delta, epsilon, gamma, and mu, respectively. The different classes of immunoglobulins have different and well known subunit structures and three-dimensional configurations. Antibodies can be naked or conjugated to other molecules such as toxins, radioisotopes, etc.

The term "monoclonal antibodies," as used herein, refers to antibodies that are produced by a single clone of B-cells and bind to the same epitope. In contrast, the term "polyclonal antibodies" refers to a population of antibodies that are produced by different B-cells and bind to different epitopes of the same antigen.

The term "antibody fragment" refers to a portion of an intact antibody. An "antigen-binding fragment," "antigen-binding domain," or "antigen-binding region," refers to a portion of an intact antibody that binds to an antigen. An antigen-binding fragment can contain the antigenic determining regions of an intact antibody (e.g., the complementarity determining regions (CDR)). Examples of antigen-binding fragments of antibodies include, but are not limited to Fab, Fab', F(ab')2, and Fv fragments, linear antibodies, and single chain antibodies. An antigen-binding fragment of an antibody can be derived from any animal species, such as rodents (e.g., mouse, rat, or hamster) and humans or can be artificially produced.

A whole antibody typically consists of four polypeptides: two identical copies of a heavy (H) chain polypeptide and two identical copies of a light (L) chain polypeptide. Each of the heavy chains contains one N-terminal variable (VH) region and three C-terminal constant (CHI, CH2 and CH3) regions, and each light chain contains one N-terminal variable (VL) region and one C-terminal constant (CL) region. The variable regions of each pair of light and heavy chains form the antigen binding site of an antibody. The VH and VL regions have the same general structure, with each region comprising four framework regions, whose sequences are relatively conserved. The term "framework region," as used herein, refers to the relatively conserved amino acid sequences within the variable region which are located between the hypervariable or complementary determining regions (CDRs). There are four framework regions in each variable domain, which are designated FR1, FR2, FR3, and FR4. The framework regions form the β sheets that provide the structural framework of the variable region (see, e.g., C. A. Janeway et al. (eds.), *Immunobiology*, 5th Ed., Garland Publishing, New York, NY (2001)). The three CDRs, known as CDR1, CDR2, and CDR3, form the "hypervariable region" of an antibody, which is responsible for antigen binding.

The terms "VL" and "VL domain" are used interchangeably to refer to the light chain variable region of an antibody.

The terms "VH" and "VH domain" are used interchangeably to refer to the heavy chain variable region of an antibody.

The term "Kabat numbering" and like terms are recognized in the art and refer to a system of numbering amino acid residues in the heavy and light chain variable regions of an antibody or an antigen-binding fragment thereof. In certain aspects, CDRs can be determined according to the Kabat numbering system (see, e.g., Kabat E A & Wu T T (1971) Ann NY Acad Sci 190: 382-391 and Kabat E A et al., (1991) Sequences of Proteins of Immunological Interest, Fifth Edition, U.S. Department of Health and Human Services, NIH Publication No. 91-3242). Using the Kabat numbering system, CDRs within an antibody heavy chain molecule are typically present at amino acid positions 31 to 35, which optionally can include one or two additional amino acids, following 35 (referred to in the Kabat numbering scheme as 35A and 35B) (CDR1), amino acid positions 50 to 65 (CDR2), and amino acid positions 95 to 102 (CDR3). Using the Kabat numbering system, CDRs within an antibody light chain molecule are typically present at amino acid positions 24 to 34 (CDR1), amino acid positions 50 to 56 (CDR2), and amino acid positions 89 to 97 (CDR3). In a specific embodiment, the CDRs of the antibodies described herein have been determined according to the Kabat numbering scheme.

Chothia refers instead to the location of the structural loops (Chothia and Lesk, J. Mol. Biol. 196:901-917 (1987)). The end of the Chothia CDR-H1 loop when numbered using the Kabat numbering convention varies between H32 and H34 depending on the length of the loop (this is because the Kabat numbering scheme places the insertions at H35A and H35B; if neither 35A nor 35B is present, the loop ends at 32; if only 35A is present, the loop ends at 33; if both 35A and 35B are present, the loop ends at 34). The AbM hypervariable regions represent a compromise between the Kabat CDRs and Chothia structural loops, and are used by Oxford Molecular's AbM antibody modeling software.

| Loop | Kabat | AbM | Chothia |
|------|-------|-----|---------|
| L1 | L24-L34 | L24-L34 | L24-L34 |
| L2 | L50-L56 | L50-L56 | L50-L56 |
| L3 | L89-L97 | L89-L97 | L89-L97 |
| H1 | H31-H35B | H26-H35B | H26-H32..34 |
| | | (Kabat Numbering) | |
| H1 | H31-H35 | H26-H35 | H26-H32 |
| | | (Chothia Numbering) | |
| H2 | H50-H65 | H50-H58 | H52-H56 |
| H3 | H95-H102 | H95-H102 | H95-H102 |

As used herein, the term "constant region" or "constant domain" are interchangeable and have its meaning common in the art. The constant region is an antibody portion, e.g., a carboxyl terminal portion of a light and/or heavy chain which is not directly involved in binding of an antibody to antigen but which can exhibit various effector functions, such as interaction with the Fc receptor. The constant region of an immunoglobulin molecule generally has a more conserved amino acid sequence relative to an immunoglobulin variable domain.

As used herein, the term "heavy chain" when used in reference to an antibody can refer to any distinct type, e.g., alpha (α), delta (δ), epsilon (ε), gamma (γ), and mu (μ), based on the amino acid sequence of the constant domain, which give rise to IgA, IgD, IgE, IgG, and IgM classes of antibodies, respectively, including subclasses of IgG, e.g., $IgG_1$, $IgG_2$, $IgG_3$, and $IgG_4$. Heavy chain amino acid sequences are well known in the art. In specific embodiments, the heavy chain is a human heavy chain.

As used herein, the term "light chain" when used in reference to an antibody can refer to any distinct type, e.g., kappa (κ) or lambda (λ) based on the amino acid sequence of the constant domains. Light chain amino acid sequences are well known in the art. In specific embodiments, the light chain is a human light chain.

A "chimeric" antibody refers to an antibody or fragment thereof comprising both human and non-human regions. A "humanized" antibody is an antibody comprising a human antibody scaffold and at least one CDR obtained or derived from a non-human antibody. Non-human antibodies include antibodies isolated from any non-human animal, such as, for example, a rodent (e.g., a mouse or rat). A humanized antibody can comprise, one, two, or three CDRs obtained or derived from a non-human antibody. A fully human antibody does not contain any amino acid residues obtained or derived from a non-human animal. It will be appreciated that fully human and humanized antibodies carry a lower risk for inducing immune responses in humans than mouse or chimeric antibodies (see, e.g., Harding et al., *mAbs*, 2(3): 256-26 (2010)).

As used herein, an "epitope" is a term in the art and refers to a localized region of an antigen to which an antibody or antigen-binding fragment thereof can specifically bind. An epitope can be, for example, contiguous amino acids of a polypeptide (linear or contiguous epitope) or an epitope can, for example, come together from two or more non-contiguous regions of a polypeptide or polypeptides (conformational, non-linear, discontinuous, or non-contiguous epitope). In certain embodiments, the epitope to which an antibody or antigen-binding fragment thereof binds can be determined by, e.g., NMR spectroscopy, X-ray diffraction crystallography studies, ELISA assays, hydrogen/deuterium exchange coupled with mass spectrometry (e.g., liquid chromatography electrospray mass spectrometry), array-based oligo-peptide scanning assays, and/or mutagenesis mapping (e.g., site-directed mutagenesis mapping). For X-ray crystallography, crystallization can be accomplished using any of the known methods in the art (e.g., Giegé R et al., (1994) Acta Crystallogr D Biol Crystallogr 50 (Pt 4): 339-350; McPherson A (1990) Eur J Biochem 189: 1-23; Chayen N E (1997) Structure 5: 1269-1274; McPherson A (1976) J Biol Chem 251: 6300-6303). Antibody/antigen-binding fragment thereof: antigen crystals can be studied using well known X-ray diffraction techniques and can be refined using computer software such as X-PLOR (Yale University, 1992, distributed by Molecular Simulations, Inc.; see, e.g., Meth Enzymol (1985) volumes 114 & 115, eds Wyckoff H W et al.,; U.S. 2004/0014194), and BUSTER (Bricogne G (1993) Acta Crystallogr D Biol Crystallogr 49(Pt 1): 37-60; Bricogne G (1997) Meth Enzymol 276A: 361-423, ed Carter C W; Roversi P et al., (2000) Acta Crystallogr D Biol Crystallogr 56 (Pt 10): 1316-1323). Mutagenesis mapping studies can be accomplished using any method known to one of skill in the art. See, e.g., Champe M et al., (1995) J Biol Chem 270: 1388-1394 and Cunningham B C & Wells J A (1989) Science 244: 1081-1085 for a description of mutagenesis techniques, including alanine scanning mutagenesis techniques.

An antibody that "binds to the same epitope" as a reference antibody refers to an antibody that binds to the same amino acid residues as the reference antibody. The ability of an antibody to bind to the same epitope as a reference antibody can determined by a hydrogen/deuterium exchange assay (see Coales et al. Rapid Commun. Mass Spectrom. 2009; 23: 639-647) or x-ray crystallography.

As used herein, the terms "immunospecifically binds," "immunospecifically recognizes," "specifically binds," and "specifically recognizes" are analogous terms in the context of antibodies or antigen-binding fragments thereof. These terms indicate that the antibody or antigen-binding fragment thereof binds to an epitope via its antigen-binding domain and that the binding entails some complementarity between the antigen binding domain and the epitope. Accordingly, for example, an antibody that "specifically binds" to a first *S. aureus* leukotoxin may also bind to other *S. aureus* leukotoxins, but the extent of binding to an un-related, non-leukotoxin protein is less than about 10% of the binding of the antibody to the first *S. aureus* leukotoxin as measured, e.g., by a radioimmunoassay (RIA), enzyme-linked immunosorbent assay (ELISA), BiaCore or an octet binding assay.

An antibody is said to "competitively inhibit" binding of a reference antibody to a given epitope if it preferentially binds to that epitope or an overlapping epitope to the extent that it blocks, to some degree, binding of the reference antibody to the epitope. Competitive inhibition may be determined by any method known in the art, for example, competition ELISA assays. An antibody may be said to competitively inhibit binding of the reference antibody to a given epitope by at least 90%, at least 80%, at least 70%, at least 60%, or at least 50%.

The term "nucleic acid sequence" is intended to encompass a polymer of DNA or RNA, i.e., a polynucleotide, which can be single-stranded or double-stranded and which can contain non-natural or altered nucleotides. The terms "nucleic acid" and "polynucleotide" as used herein refer to a polymeric form of nucleotides of any length, either ribonucleotides (RNA) or deoxyribonucleotides (DNA). These terms refer to the primary structure of the molecule, and thus include double- and single-stranded DNA, and double- and single-stranded RNA. The terms include, as equivalents, analogs of either RNA or DNA made from nucleotide analogs and modified polynucleotides such as, though not limited to, methylated and/or capped polynucleotides. Nucleic acids are typically linked via phosphate bonds to form nucleic acid sequences or polynucleotides, though many other linkages are known in the art (e.g., phosphorothioates, boranophosphates, and the like).

"Transfection," "transformation," or "transduction," as used herein, refer to the introduction of one or more exogenous polynucleotides into a host cell by using physical or chemical methods. Many transfection techniques are known in the art and include, for example, calcium phosphate DNA co-precipitation (see, e.g., Murray E. J. (ed.), *Methods in Molecular Biology, Vol. 7, Gene Transfer and Expression Protocols*, Humana Press (1991)); DEAE-dextran; electroporation; cationic liposome-mediated transfection; tungsten particle-facilitated microparticle bombardment (Johnston, *Nature*, 346: 776-777 (1990)); and strontium phosphate DNA co-precipitation (Brash et al, *Mol. Cell Biol.*, 7: 2031-2034 (1987)). Phage or viral vectors can be introduced into host cells, after growth of infectious particles in suitable packaging cells, many of which are commercially available.

As used herein, the terms "treatment," "treating," and the like, refer to measures (e.g., administration of an antibody or antigen-binding fragment thereof provided herein to a subject) that cure, slow down, lessen symptoms of, and/or halt progression of a diagnosed pathologic condition or disorder. Thus, those in need of treatment include those already diagnosed with or suspected of having the disorder. A "therapeutically effective amount" refers to an amount effective, at dosages and for periods of time necessary, to achieve a desired therapeutic result (e.g., treatment of *S. aureus* infection).

Prophylactic or preventative measures refer to measures (e.g., administration of an antibody or antigen-binding fragment thereof provided herein to a subject) that prevent and/or slow the development of a targeted pathologic condition or disorder. Thus, those in need of prophylactic or preventative measures include those prone to have the disorder and those in whom the disorder is to be prevented. A "prophylactically effective amount" refers to an amount effective, at dosages and for periods of time necessary, to achieve a desired prophylactic result (e.g., prevention of *S. aureus* infection or disease onset).

A subject "colonized" with *S. aureus* refers to a subject with *S. aureus* present in or on the body. Colonization can be determined, for example, by detecting *S. aureus* in a sample obtained from the subject. The *S. aureus* can be detected, e.g., by culturing or by polymerase chain reaction (PCR). Infections that result from or that are attendant to the presence of *S. aureus* in or on the body of a subject show radiographic and/or clinical signs of the bacteria. An *S. aureus* infection can occur, for example, as a skin or soft tissue infection (SSTI) or bacteremia. *S. aureus* bacteria can travel through the bloodstream and infect a site in the body, resulting in pneumonia, ICU pneumonia, a bone or joint infection, a device infection, a wound infection, a surgical site infection, or osteomyelitis. Radiographic signs include, for example, X-rays showing infiltrates. Clinical signs include, for example, abnormal temperature, abnormal white blood cell count, cough, purulent sputum, bronchial breath sounds, dyspnea, tachypnea (respiratory rate>30 breaths/minute), and/or hypoxemia.

The terms "administer", "administering", "administration", and the like, as used herein, refer to methods that may be used to enable delivery of a drug, e.g., a combination of anti-*S. aureus* antibodies or antigen-binding fragments thereof to the desired site of biological action (e.g., intravenous administration). Administration techniques that can be employed with the agents and methods described herein are found in e.g., Goodman and Gilman, *The Pharmacological Basis of Therapeutics*, current edition, Pergamon; and Remington's, *Pharmaceutical Sciences*, current edition, Mack Publishing Co., Easton, Pa.

Administration "in combination with" one or more further therapeutic agents includes simultaneous (concurrent) or consecutive administration in any order.

Unless specifically stated or obvious from context, as used herein, the term "or" is understood to be inclusive. The term "and/or" as used in a phrase such as "A and/or B" herein is intended to include both "A and B," "A or B," "A," and "B." Likewise, the term "and/or" as used in a phrase such as "A, B, and/or C" is intended to encompass each of the following embodiments: A, B, and C; A, B, or C; A or C; A or B; B or C; A and C; A and B; B and C; A (alone); B (alone); and C (alone).

II. Anti-*Staphylococcus aureus* Alpha Toxin Antibodies

As provided herein, antibodies and antigen-binding fragments thereof (e.g., monoclonal antibodies and fragments)

that bind to *S. aureus* alpha toxin can be used to avoid *S. aureus* infections in subjects colonized with a low level of *S. aureus*.

Alpha toxin (AT) is a key virulence factor in several *S. aureus* diseases, including pneumonia, skin and soft tissue infections (SSTI), and bacteremia (Bubeck Wardenburg, J. and O. Schneewind, *J. Exp. Med.,* 205: 287-294 (2008); Inoshima et al., *J. Invest. Dermatol.,* 132: 1513-1516 (2012); and Foletti et al., supra). Passive immunization with anti-AT monoclonal antibodies reduced disease severity in pneumonia and dermonecrosis models (Hua et al., *Antimicrob. Agents Chemother.,* 58: 1108-1117 (2014); Tkaczyk et al., *Clin. Vaccine Immunol.,* 19: 377-385 (2012); and Ragle, B. E. and J. Wardenburg Bubeck, *Infect. Immun.,* 77: 2712-2718 (2009)), and vaccination with an AT toxoid containing an H35L mutation (ATH35L) protected against death in mouse lethal bacteremia and pneumonia models (Bubeck Wardenburg, supra, Foletti et al., supra, Hua et al., supra, Ragle, supra, Menzies, B. E. and D. S Kernodle, *Infect. Immun.,* 77: 2712-2718 (2009); and Adhikari et al., *PLoS One,* 7: e38567 (2012)). AT contributes to multiple aspects of *S. aureus* pathogenesis during bacteremia and sepsis, including stimulating a hyperinflammatory response characteristic of sepsis and activating ADAM10-mediated cleavage of endothelial tight junctions, leading to a loss in vascular integrity (Powers et al., *J Infect. Dis.,* 206: 352-356 (2012); Wilke, G. A. and J. Bubeck Wardenburg, *Proc. Natl. Acad. Sci. USA,* 107: 13473-13478 (2010); and Becker et al., *J Innate Immun.,* 6: 619-631 (2014)). AT also has been demonstrated to target platelets, which prevents repair of the injured endothelial barrier and promotes organ dysfunction through platelet-neutrophil aggregate formation (Powers et al., *Cell Host Microbe,* 17: 775-787 (2015)). Alpha toxin structure and function is described in detail in, for example, Bhakdi, S. and J. Tranum-Jensen, *Microbiol. Mol. Biol. Rev.,* 55(4): 733-751 (1991).

Monoclonal and polyclonal antibodies that bind AT are known in the art (see, e.g., Hua et al., *Antimicrob. Agents Chemother.,* 58(2): 1108-1117 (2014); and Oganesyan et al., *J. Biol. Chem.,* 289: 29874-29880 (2014)) and are commercially available from sources such as, for example, Sigma Aldrich (St. Louis, MO) and AbCam (Cambridge, MA). Exemplary antibodies that bind to AT are disclosed, for example, in WO 2012/109285 and WO 2014/074540 (both of which are herein incorporated by reference in their entireties).

In one instance, an antibody or antigen-binding fragment (e.g., monoclonal antibody or fragment) that specifically binds to *S. aureus* alpha toxin (AT) comprises, consists essentially of, or consists of (i) a heavy chain polypeptide comprising a CDR1 amino acid sequence of SEQ ID NO:1, a CDR2 amino acid sequence of SEQ ID NO:2, and a CDR3 amino acid sequence of SEQ ID NO:3, and (ii) a light chain polypeptide comprising a CDR1 amino acid sequence of SEQ ID NO:4, a CDR2 amino acid sequence of SEQ ID NO:5, and a CDR3 amino acid sequence of SEQ ID NO:6. In another instance, the heavy chain polypeptide of an antibody or antigen-binding fragment (e.g., monoclonal antibody or fragment) that specifically binds to *S. aureus* AT comprises, consists essentially of, or consists of a variable region amino acid sequence of SEQ ID NO:7. In another instance, the light chain polypeptide of an antibody or antigen-binding fragment (e.g., monoclonal antibody or fragment) that specifically binds to *S. aureus* AT comprises, consists essentially of, or consists of a variable region amino acid sequence of SEQ ID NO:8. In another instance, an antibody or antigen-binding fragment (e.g., monoclonal antibody or fragment) that specifically binds to *S. aureus* AT comprises, consists essentially of, or consists of a variable heavy chain comprising, consisting essentially of, or consisting of the amino acid sequence of SEQ ID NO:7 and a light chain variable region comprising, consisting essentially of, or consisting of the amino acid sequence of SEQ ID NO:8. In another instance, an antibody or antigen-binding fragment (e.g., monoclonal antibody or fragment) that specifically binds to *S. aureus* AT comprises, consists essentially of, or consists of a heavy chain comprising, consisting essentially of, or consisting of the amino acid sequence of SEQ ID NO:9 and/or a light chain variable region comprising, consisting essentially of, or consisting of the amino acid sequence of SEQ ID NO:10.

Sequences of exemplary anti-AT antibodies are provided below. Additional anti-AT antibodies are provided, for example, in U.S. Pat. No. 9,527,905, which is herein incorporated by reference in its entirety. In certain instances, an antibody or antigen-binding fragment thereof described herein binds to AT and comprises the six CDRs of an antibody listed in the two tables below (i.e., the three VH CDRs of the antibody listed in the first table and the three VL CDRs of the same antibody listed in the second table).

The anti-AT antibody MEDI4893 (also known as suvratoxumab) is a human monoclonal antibody with an extended half-life that binds AT with high affinity and effectively blocks AT pore formation in target cell membranes. Half-life extension was achieved with introduction of three amino acid substitutions (M252Y/S254T/T256E; called YTE) in the Fc domain to increase binding to the neonatal Fc receptor (FcRn) and consequently increase the serum half-life. Because YTE mutations decrease antibody half-life and exposure in mice, an identical version of MEDI4893, with the exception of the YTE modification, referred to as MEDI4893* or "LC10" has been utilized to demonstrate efficacy in preclinical models, as described previously in International Patent Application Publications WO 2012/109285 and WO 2014/074540 (both of which are herein incorporated by reference in their entireties). MEDI4893 (or suvratoxumab) contains a heavy chain with the amino acid sequence set forth in SEQ ID NO:9 and a light chain with the amino acid sequence set forth in SEQ ID NO:10. The identical CDR, VH and VL sequences of MEDI4893 (suvratoxumab) and MEDI4893* are provided in the tables below.

VH CDR Amino Acid Sequences

| Antibody Name | VH CDR1 (SEQ ID NO: 1) | VH CDR2 (SEQ ID NO: 2) | VH CDR3 (SEQ ID NO: 3) |
|---|---|---|---|
| MEDI4893 or MEDI4893* | SHDMH (SEQ ID NO: 1) | GIGTAGDT YYPDSVKG (SEQ ID NO: 2) | DRYSPTGHYYGMDV (SEQ ID NO: 3) |

VL CDR Amino Acid Sequences

| Antibody | VL CDR1 (SEQ ID NO: 4) | VL CDR2 (SEQ ID NO: 5) | VL CDR3 (SEQ ID NO: 6) |
|---|---|---|---|
| MEDI4893 or MEDI4893* | RASQSISSWLA (SEQ ID NO: 4) | KASSLES (SEQ ID NO: 5) | KQYADYWT (SEQ ID NO: 6) |

In certain instances, an antibody or antigen-binding fragment thereof described herein binds to AT and comprises the VH of an antibody listed in the following table, e.g., in combination with a VL.

| Variable Heavy Chain (VH) Amino Acid Sequence | |
|---|---|
| Antibody | VH Amino Acid Sequence (SEQ ID NO: 7) |
| MEDI4893 or MEDI4893* | EVQLVESGGGLVQPGGSLRLSCAASGFTFSSHDMHWVRQ ATGKGLEWVSGIGTAGDTYYPDSVKGRFTISRENAKNSL YLQMNSLRAGDTAVYYCARDRYSPTGHYYGMDVWGQGTT VTVSS (SEQ ID NO: 7) |

In certain instances, an antibody or antigen-binding fragment thereof described herein binds to AT and comprises the VL of an antibody listed in the following table, e.g., in combination with a VH, optionally the VH of the same antibody listed in the preceding table.

| Variable Light Chain (VL) Amino Acid Sequence | |
|---|---|
| Antibody | VL Amino Acid Sequence (SEQ ID NO: 8) |
| MEDI4893 or MEDI4893* | DIQMTQSPSTLSASVGDRVTITCRASQSISSWLAWYQQK PGKAPKLLIYKASSLESGVPSRFSGSGSGTEFTLTISSL QPDDFATYYCKQYADYWTFGQGTKVEIK (SEQ ID NO: 8) |

In certain instances, an antibody or antigen-binding fragment thereof described herein binds to AT and comprises the heavy chain of an antibody listed in the following table, e.g., in combination with a light chain.

| Full-length heavy chain amino acid sequences | |
|---|---|
| Antibody | Full-Length Heavy Chain Amino Acid Sequence |
| MEDI4893 | EVQLVESGGGLVQPGGSLRLSCAASGFTFSSHDMEIWV RQATGKGLEWVSGIGTAGDTYYPDSVKGRFTISRENAK NSLYLQMNSLRAGDTAVYYCARDRYSPTGHYYGMDVWG QGTTVTVSSASTKGPSVFPLAPSSKSTSGGTAALGCLV KDYFPEPVTVSWNSGALTSGVHTFPAVLQSSGLYSLSS VVTVPSSSLGTQTYICNVNHKPSNTKVDKRVEPKSCDK THTCPPCPAPELLGGPSVFLFPPKPKDTLYITREPEVT CVVVDVSHEDPEVKFNWYVDGVEVHNAKTKPREEQYNS TYRVVSVLTVLHQDWLNGKEYKCKVSNKALPAPIEKTI SKAKGQPREPQVYTLPPSREEMTKNQVSLTCLVKGFYP SDIAVEWESNGQPENNYKTTPPVLDSDGSFFLYSKLTV DKSRWQQGNVFSCSVMHEALHNHYTQKSLSLSPGK (SEQ ID NO: 9) |
| MEDI4893* | EVQLVESGGGLVQPGGSLRLSCAASGFTFSSHDMEIWV RQATGKGLEWVSGIGTAGDTYYPDSVKGRFTISRENAK NSLYLQMNSLRAGDTAVYYCARDRYSPTGHYYGMDVWG QGTTVTVSSASTKGPSVFPLAPSSKSTSGGTAALGCLV KDYFPEPVTVSWNSGALTSGVHTFPAVLQSSGLYSLSS VVTVPSSSLGTQTYICNVNHKPSNTKVDKRVEPKSCDK THTCPPCPAPELLGGPSVFLFPPKPKDTLMISRTPEVT CVVVDVSHEDPEVKFNWYVDGVEVHNAKTKPREEQYNS TYRVVSVLTVLHQDWLNGKEYKCKVSNKALPAPIEKTI SKAKGQPREPQVYTLPPSREEMTKNQVSLTCLVKGFYP SDIAVEWESNGQPENNYKTTPPVLDSDGSFFLYSKLTV DKSRWQQGNVFSCSVMHEALHNHYTQKSLSLSPGK (SEQ ID NO: 11) |

In certain instances, an antibody or antigen-binding fragment thereof described herein binds to AT and comprises the light chain of an antibody listed in the following table, e.g., in combination with a heavy chain, optionally the heavy chain of the same antibody listed in the preceding table.

| Full-length light chain amino acid sequences | |
|---|---|
| Antibody | Full-Length Light Chain Amino Acid Sequence (SEQ ID NO: 10) |
| MEDI4893 or MEDI4893* | DIQMTQSPSTLSASVGDRVTITCRASQSISSWLAWYQQK PGKAPKLLIYKASSLESGVPSRFSGSGSGTEFTLTISSL QPDDFATYYCKQYADYWTFGQGTKVEIKRTVAAPSVFIF PPSDEQLKSGTASVVCLLNNFYPREAKVQWKVDNALQSG NSQESVTEQDSKDSTYSLSSTLTLSKADYEKHKVYACEV THQGLSSPVTKSFNRGE (SEQ ID NO: 10) |

In certain aspects, the CDRs of an antibody or antigen-binding fragment thereof can be determined according to the Chothia numbering scheme, which refers to the location of immunoglobulin structural loops (see, e.g., Chothia C & Lesk A M, (1987), J Mol Biol 196: 901-917; Al-Lazikani B et al., (1997) J Mol Biol 273: 927-948; Chothia C et al., (1992) J Mol Biol 227: 799-817; Tramontano A et al., (1990) J Mol Biol 215(1): 175-82; and U.S. Pat. No. 7,709,226). Typically, when using the Kabat numbering convention, the Chothia CDR-H1 loop is present at heavy chain amino acids 26 to 32, 33, or 34, the Chothia CDR-H2 loop is present at heavy chain amino acids 52 to 56, and the Chothia CDR-H3 loop is present at heavy chain amino acids 95 to 102, while the Chothia CDR-L1 loop is present at light chain amino acids 24 to 34, the Chothia CDR-L2 loop is present at light chain amino acids 50 to 56, and the Chothia CDR-L3 loop is present at light chain amino acids 89 to 97. The end of the Chothia CDR-H1 loop when numbered using the Kabat numbering convention varies between H32 and H34 depending on the length of the loop (this is because the Kabat numbering scheme places the insertions at H35A and H35B; if neither 35A nor 35B is present, the loop ends at 32; if only 35A is present, the loop ends at 33; if both 35A and 35B are present, the loop ends at 34).

In certain aspects, provided herein are combinations of antibodies and antigen-binding fragments thereof that comprise the Chothia VH and VL CDRs of the MEDI4893 antibody. In certain embodiments, antibodies or antigen-binding fragments thereof comprise one or more CDRs, in which the Chothia and Kabat CDRs have the same amino acid sequence. In certain embodiments, provided herein are antibodies and antigen-binding fragments thereof comprise combinations of Kabat CDRs and Chothia CDRs.

In certain aspects, the CDRs of an antibody or antigen-binding fragment thereof can be determined according to the IMGT numbering system as described in Lefranc M-P, (1999) The Immunologist 7: 132-136 and Lefranc M-P et al., (1999) Nucleic Acids Res 27: 209-212. According to the IMGT numbering scheme, VH-CDR1 is at positions 26 to 35, VH-CDR2 is at positions 51 to 57, VH-CDR3 is at positions 93 to 102, VL-CDR1 is at positions 27 to 32, VL-CDR2 is at positions 50 to 52, and VL-CDR3 is at positions 89 to 97. In a particular embodiment, provided herein are combinations of antibodies and antigen-binding fragments thereof that comprise the IMGT VH and VL CDRs of MEDI4893, for example, as described in Lefranc M-P (1999) supra and Lefranc M-P et al., (1999) supra).

In certain aspects, the CDRs of an antibody or antigen-binding fragment thereof can be determined according to MacCallum R M et al., (1996) J Mol Biol 262: 732-745. See also, e.g., Martin A. "Protein Sequence and Structure Analysis of Antibody Variable Domains," in *Antibody Engineering*, Kontermann and Dübel, eds., Chapter 31, pp. 422-439, Springer-Verlag, Berlin (2001). In a particular embodiment, provided herein are combinations of antibodies or antigen-binding fragments thereof comprise the VH and VL CDRs of the MEDI4893 antibody determined by the method in MacCallum R M et al.

In certain aspects, the CDRs of an antibody or antigen-binding fragment thereof can be determined according to the AbM numbering scheme, which refers AbM hypervariable regions which represent a compromise between the Kabat CDRs and Chothia structural loops, and are used by Oxford Molecular's AbM antibody modeling software (Oxford Molecular Group, Inc.). In a particular embodiment, provided herein are combinations of antibodies or antigen-binding fragments that and comprise VH and VL CDRs of the MEDI4893 antibody as determined by the AbM numbering scheme.

In another aspect, the antibody or antigen-binding fragment thereof (e.g., monoclonal antibody or fragment) described herein can comprise a constant region (Fc) of any suitable class (e.g., IgG, IgA, IgD, IgM, and IgE) that has been modified in order to improve the half-life of the antibody or antigen-binding fragment (e.g., monoclonal antibody or fragment). For example, the antibody or antigen-binding fragment thereof (e.g., monoclonal antibody or fragment) described herein can comprise an Fc that comprises a mutation that extends half-life relative to the same antibody without the mutation.

Fc region engineering is widely used in the art to extend the half-life of therapeutic antibodies and protect from degradation in vivo. In some embodiments, the Fc region of an IgG antibody or antigen-binding fragment can be modified in order to increase the affinity of the IgG molecule for the Fc Receptor-neonate (FcRn), which mediates IgG catabolism and protects IgG molecules from degradation. Suitable Fc region amino acid substitutions or modifications are known in the art and include, for example, the triple substitution M252Y/S254T/T256E (referred to as "YTE") (see, e.g., U.S. Pat. No. 7,658,921; U.S. Patent Application Publication 2014/0302058; and Yu et al., *Antimicrob. Agents Chemother.*, 61(1): e01020-16 (2017)). In certain aspects, an antibody or antigen-binding binding fragment (e.g., monoclonal antibody or fragment) that binds to *S. aureus* AT comprises an Fc region comprising the YTE mutation.

An antibody or antigen-binding fragment (e.g. monoclonal antibody or fragment) described herein can be, or can be obtained from, a human antibody, a humanized antibody, a non-human antibody, or a chimeric antibody. In one aspect, an antibody described herein, or antigen-binding fragment thereof, is a fully human antibody.

A human antibody, a non-human antibody, a chimeric antibody, or a humanized antibody can be obtained by any means, including via in vitro sources (e.g., a hybridoma or a cell line producing an antibody recombinantly) and in vivo sources (e.g., rodents, human tonsils). Methods for generating antibodies are known in the art and are described in, for example, Köhler and Milstein, *Eur. J. Immunol.*, 5: 511-519 (1976); Harlow and Lane (eds.), *Antibodies: A Laboratory Manual*, CSH Press (1988); and Janeway et al. (eds.), *Immunobiology*, 5th Ed., Garland Publishing, New York, NY (2001)). In certain embodiments, a human antibody or a chimeric antibody can be generated using a transgenic animal (e.g., a mouse) wherein one or more endogenous immunoglobulin genes are replaced with one or more human immunoglobulin genes. Examples of transgenic mice wherein endogenous antibody genes are effectively replaced with human antibody genes include, but are not limited to, the Medarex HUMAB-MOUSE™, the Kirin TC MOUSE™, and the Kyowa Kirin KM-MOUSE™ (see, e.g., Lonberg, *Nat. Biotechnol.*, 23(9): 1117-25 (2005), and Lonberg, *Handb. Exp. Pharmacol.*, 181: 69-97 (2008)). A humanized antibody can be generated using any suitable method known in the art (see, e.g., An, Z. (ed.), *Therapeutic Monoclonal Antibodies: From Bench to Clinic*, John Wiley & Sons, Inc., Hoboken, NJ (2009)), including, e.g., grafting of non-human CDRs onto a human antibody scaffold (see, e.g., Kashmiri et al., *Methods*, 36(1): 25-34 (2005); and Hou et al., *J. Biochem.*, 144(1): 115-120 (2008)). In one embodiment, a humanized antibody can be produced using the methods described in, e.g., U.S. Patent Application Publication 2011/0287485 A1.

III. Nucleic Acids, Vectors, and Host Cells

Also provided herein are one or more isolated nucleic acid sequences that encode the antibody or antigen-binding fragment thereof that binds to AT, (optionally wherein the antibody or antigen-binding fragment is a monoclonal antibody or fragment).

The disclosure further provides one or more vectors comprising one or more nucleic acid sequences encoding an antibody or antigen-binding fragment thereof that binds to AT (optionally wherein the antibody or antigen-binding fragment is a monoclonal antibody or fragment). The vector can be, for example, a plasmid, episome, cosmid, viral vector (e.g., retroviral or adenoviral), or phage.

The vector(s) comprising the nucleic acid(s) encoding the antibody or antigen-binding fragment thereof that binds to AT (optionally wherein the antibody or antigen-binding fragment is a monoclonal antibody or fragment) can be introduced into a host cell that is capable of expressing the polypeptides encoded thereby, including any suitable prokaryotic or eukaryotic cell. As such, the present disclosure provides an isolated cell comprising the vector. Host cells that may be used include those that can be easily and reliably grown, have reasonably fast growth rates, have well characterized expression systems, and can be transformed or transfected easily and efficiently.

A nucleic acid sequence encoding amino acids of any of the antibodies or antigen-binding fragments (optionally monoclonal antibodies or fragments) described herein can be introduced into a cell by transfection, transformation, or transduction.

IV. Pharmaceutical Compositions and Methods of Administering Anti-AT Antibodies

The present disclosure provides a composition comprising an effective amount of any the anti-AT antibodies or antigen-binding fragments thereof described herein and a pharmaceutically acceptable carrier. The amount can be effective to decrease the risk of infection in a subject colonized with *S. aureus.*

In another aspect, the composition may comprise nucleic acid sequences encoding the AT-binding antibody or antigen-binding fragment. The nucleic acid sequences can be present in a vector or combination of vectors.

In one aspect, the composition is a pharmaceutically acceptable (e.g., physiologically acceptable) composition, which comprises a carrier, such as a pharmaceutically acceptable (e.g., physiologically acceptable) carrier and the AT-binding antibody or antigen-binding fragment nucleic acid sequence(s), or vector(s).

Any suitable carrier can be used within the context of the disclosure, and such carriers are well known in the art. The choice of carrier will be determined, in part, by the particular site to which the composition may be administered and the particular method used to administer the composition. The composition optionally can be sterile. The composition can be frozen or lyophilized for storage and reconstituted in a suitable sterile carrier prior to use. The compositions can be generated in accordance with conventional techniques described in, e.g., *Remington: The Science and Practice of Pharmacy,* 21st Edition, Lippincott Williams & Wilkins, Philadelphia, PA (2001).

The composition desirably comprises the AT-binding antibody or antigen-binding fragment in an amount that is effective to decrease the risk of *S. aureus* infection in a patient that is colonized with *S. aureus*. To this end, the disclosed methods comprise administering a therapeutically effective amount or prophylactically effective amount of an AT-binding antibody or antigen-binding fragment thereof or a composition the aforementioned antibodies or fragments (including monoclonal antibodies or fragments).

For repeated administrations over several days or longer, depending on the condition, the treatment can be repeated until a desired suppression of disease symptoms occurs. However, other dosage regimens may be useful and are within the scope of the present disclosure. The desired dosage can be delivered by a single bolus administration of the composition, by multiple bolus administrations of the composition, or by continuous infusion administration of the composition.

An effective amount of an anti-AT antibody or antigen-binding fragment thereof, can be administered to a subject, such as a human, using standard administration techniques, including intravenous, intraperitoneal, subcutaneous, and intramuscular administration routes. The anti-AT antibody or antigen-binding fragment thereof may be suitable for parenteral administration. The term "parenteral," as used herein, includes intravenous, intramuscular, subcutaneous, and intraperitoneal administration. In some embodiments, the anti-AT antibody or antigen-binding fragment thereof is administered to a subject using peripheral systemic delivery by intravenous, intraperitoneal, or subcutaneous injection.

The AT-binding antibody or antigen-binding fragment or composition comprising same, can be administered alone or in combination with other drugs (e.g., as an adjuvant) conventionally used for treating *S. aureus* infections. The composition comprising the AT-binding antibody or antigen-binding fragment, can be used in combination with, for example, one or more antibiotics, such as a penicillinase-resistant β-lactam antibiotic (e.g., oxacillin or flucloxacillin). Gentamicin can be used to treat serious infections, such as endocarditis. Most strains of *S. aureus*, however, are now resistant to penicillin, and two in 100 people carry methicillin-resistant strains of *S. aureus* (MRSA). MRSA infections typically are treated with vancomycin, and minor skin infections can be treated with triple antibiotic ointment.

The composition comprising the AT-binding antibody or antigen-binding fragment, can be used in combination with, for example, one more anti-*S. aureus* antibodies.

V. Methods of Identifying Patients Who Will Benefit From Anti-AT Antibodies

As demonstrated herein, administration of an anti-AT antibody or antigen-binding fragment thereof to a subject that is colonized with a low level of *S. aureus*, e.g., a level of *S. aureus* that does not exceed a threshold level of *S. aureus* can decreases the incidence of infection attendant to the presence of *S. aureus* in the subject.

The amount of *S. aureus* in a subject can be determined based on the amount of *S. aureus* in a sample obtained from the subject. The sample can be, e.g., a skin or soft tissue sample. The sample can be obtained, for example, from the lower respiratory tract of the subject. The sample can be, e.g., an endotracheal aspirate, a tracheal sample, or a bronchial sample.

In certain aspects, an anti-AT antibody or antigen-binding fragment thereof is administered to a subject wherein a sample obtained from the subject has a concentration of *S. aureus* that does not exceed a certain threshold estimated as 3.2 log 10 CFU/ml (about 1600-1700 CFU/ml).

The amount of *S. aureus* in a sample obtained from a subject can be quantified using polymerase chain reaction (PCR). For example, the amount of *S. aureus* in a sample obtained from a subject can be the number can be quantified based the number of PCR cycles needed to reach a threshold signal, referred to herein as a "cycle threshold value" or "Ct value." A high Ct value (i.e., large number of PCR cycles required to reach the threshold signal) indicates a low level of *S. aureus*, whereas a low Ct value (i.e., small number of PCR cycles required to reach the threshold signal) indicates a high level of *S. aureus*.

PCR is a particularly advantageous method to quantify the amount of *S. aureus* in a sample because it can be performed rapidly and uniformly. For instance, PCR can detect the amount of *S. aureus* in a sample in 2 hours or less. Although laboratories vary substantially in their methods for bacterial culture, they would perform the PCR test using the same type of instrument making PCR output uniform across different laboratories.

PCR can be used to determine the amount of *S. aureus* in a sample based on the amplification of a single *S. aureus* gene or a combination of *S. aureus* genes. For example, the PCR can be used to detect *S. aureus* protein A gene. Detection of *S. aureus* protein A detects all *S. aureus*, regardless of their methicillin-susceptibility. However, PCR can also be used to determine whether or not the *S. aureus* is antibiotic-resistant, e.g., methicillin-resistant. For example, the PCR can be used to detect the presence of methicillin-resistance determinant (mecA) and staph chromosomal cassette (SCCmec)). Detection of both mecA and SCCmec indicates that the *S. aureus* is methicillin-resistant.

In certain aspects, an anti-AT antibody or antigen-binding fragment thereof is administered to a subject wherein a sample obtained from the subject has a level of *S. aureus* that does not exceed a maximum level of *S. aureus* that correlates to a PCR Ct value. In certain aspects, an anti-AT antibody or antigen-binding fragment thereof is administered to a subject wherein a sample obtained from the subject has a level of *S. aureus* that does not exceed a level of *S. aureus* that correlates to a PCR Ct value of about 29. In certain aspects, an anti-AT antibody or antigen-binding fragment thereof is administered to a subject wherein a sample obtained from the subject has a level of *S. aureus* that does not exceed a level of *S. aureus* that correlates to a PCR Ct value between 29 and 36.

In certain aspects, an anti-AT antibody or antigen-binding fragment thereof is administered to a subject wherein a sample obtained from the subject has a level of *S. aureus* that is at least a minimum level of *S. aureus* that correlates to a PCR Ct value. In certain aspects, an anti-AT antibody or antigen-binding fragment thereof is administered to a subject wherein a sample obtained from the subject has a level of *S. aureus* that correlates to a PCR Ct value of about 3 to about 29. In certain aspects, an anti-AT antibody or antigen-binding fragment thereof is administered to a subject wherein a sample obtained from the subject has a level of *S. aureus* that correlates to a PCR Ct value of 3 to 29.

A PCR Ct value of 29 is estimated to correspond to a concentration of about 1600 to 1700 colony forming units (CFU)/ml of S. aureus.

The methods provided herein for identifying subjects who will benefit from receiving an anti-AT antibody or antigen-binding fragment thereof can be particularly useful in mechanically ventilated subjects. Accordingly, the subject can be a mechanically ventilated subject. While overall disease incidence is relatively low around 1-2%, the incidence of Staphylococcus aureus pneumonia is much higher (over 20%) in Staphylococcus aureus colonized patients. In mechanically ventilated subjects, Staphylococcus aureus pneumonia is an early event that generally occurs within the first week after ventilation starts, so earlier administration of an anti-AT antibody or antigen-binding fragment thereof can be critical in avoiding the pneumonia. PCR-based techniques for assessing the level of S. aureus in a patient can be completed within about 2 hours, whereas culturing techniques are much slower (and also lack the precise quantitative nature of PCR-based techniques).

PCR-based techniques are also advantageous as compared to culture-based techniques for detecting S. aureus colonization because PCR-based techniques can be more sensitive in detecting the presence of S. aureus, particularly in subjects taking antibiotics. Accordingly, the subject can be taking antibiotics. In addition, in certain aspects of the methods provided herein, PCR analysis of a sample obtained from a subject indicates that the subject will benefit from receiving an anti-AT antibody or antigen-binding fragment thereof, while the sample does not contain bacteria that would grow in a culture assay used to determine the presence of S. aureus.

The following examples further illustrate the invention but, of course, should not be construed as in any way limiting its scope.

EXAMPLE 1

Staphylococcus aureus (S. aureus) pneumonia is mechanically ventilated patients is an early event that generally occurs within the first week after ventilation. Therefore, rapid identification of patients who are at risk of developing this infection could be lifesaving. While overall disease incidence is relatively low, around 1-2%, the incidence is much higher (over 20%) in patients colonized with S. aureus.

Rapid polymerase chain reaction (PCR) was analyzed as an assay for identifying at-risk patients colonized with S. aureus in their lower respiratory tract (LRT) in a Phase 2 clinical trial of mechanically ventilated patients in the Intensive Care Unit (ICU). The Xpert® MRSA/SA SSTI Assay (Cepheid, Sunnyvale, CA), was used per the product protocol to perform the PCR. This assay is a rapid, automated DNA test for simultaneously detecting Methicillin-Resistant Staphylococcus aureus (MRSA) and Staphylococcus aureus (SA) directly from skin and soft tissue specimens. The specimen is collected on a double swab, which is place in a tube containing elution reagent. Following brief vortexing, the eluted material and two single-use reagents (Reagent 1 and Reagent 2) that are provided with the assay are transferred to different, uniquely-labeled chambers of the disposable fluidic cartridge (the Xpert MRSA/SA cartridge). The cartridge is placed into the GeneExpert® DX System instrument platform, which performs hands-off real-time multiplex PCR for detection of the DNA. In this platform, additional sample preparation, amplification, and real-time detection are fully-automated and completed integrated.

The primers and probes in the Xpert MRSA/SA Assay detect nucleic acid sequences of the S. aureus protein A (spa), the gene for MecA-mediated Oxacillin resistance (mecA), and the staphylococcal cassette chromosome (SCCmec) inserted in the SA chromosomal attB site. The test incudes a sample processing control to control for adequate processing of the target bacteria and to monitor the presence of inhibitors in the PCR assay. The Probe Check Control verifies reagent rehydration, PCR tube filing in the cartridge, probe integrity, and dye stability.

The assay is depicted in FIG. 1: an endotracheal aspirate (ETA) sample was obtained from a patient, and a swab of the sample was inserted into elution reagent. The mixture was vortexed and dispensed into a cartridge. The cartridge was then inserted into a PCR instrument to initiate the test. The total hands-on time of the test is less than 2 minutes, and the entire test is complete within 75 minutes.

The PCR test produces a cycle threshold (Ct) value that represents the number of PCR cycles needed to reach a threshold signal. The Ct value is inversely related to the bacterial load: a higher number of S. aureus in a sample requires fewer cycles to reach the threshold level and therefore has a low Ct value, whereas a lower number of S. aureus in a sample requires more cycles to reach the threshold level and therefore has a higher Ct value.

EXAMPLE 2

The rapid PCR test discussed in Example 1 was used to detect the presence or absence of S. aureus and to determine whether the S. aureus is methicillin-resistant S. aureus (MRSA) by looking at three molecular targets. The first target is the S. aureus protein A (SPA), which detects all S. aureus regardless of their methicillin-susceptibility status. The second and third targets are methicillin-resistance determinant (mecA) and staph chromosomal cassette (SCCmec), which are used to detect MRSA.

The rapid PCR test was conducted on 720 patients at screening in a Phase 2 clinical trial. Out of these patients, 299 (41.5%) were colonized with S. aureus. This number is higher than the S. aureus colonization rate of the general public (25-30%), but is a reasonable number for mechanically ventilated patients in the ICU. Of the 299 patients colonized with S. aureus, 277 (92.6%) carried methicillin-sensitive S. aureus (MSSA), and 22 (7.4%) carried MRSA.

Figure 2:
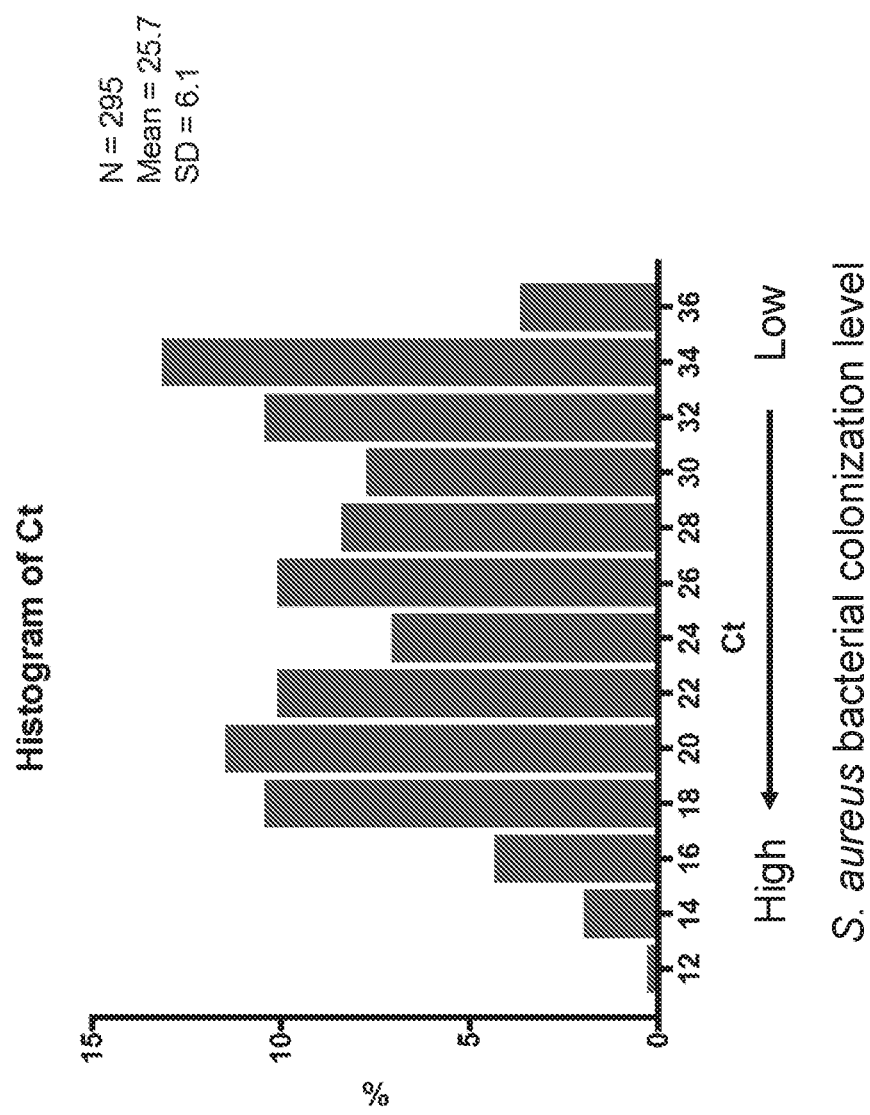
FIG. 2 is a histogram showing the Ct values obtained from patients at screening in a Phase II clinical trial. A substantial number of patients had low Ct values (high bacterial load) at screening. (See Example 2.)

Ct values for 295 of the 299 patients colonized with S. aureus are shown in FIG. 2. (4 PCR+ patients with Ct values equal to zero or missing are not shown.) The mean Ct value in these patients was 25.7, and a substantial number of the patients had low Ct values (high bacterial loads) at screening.

Figure 3:
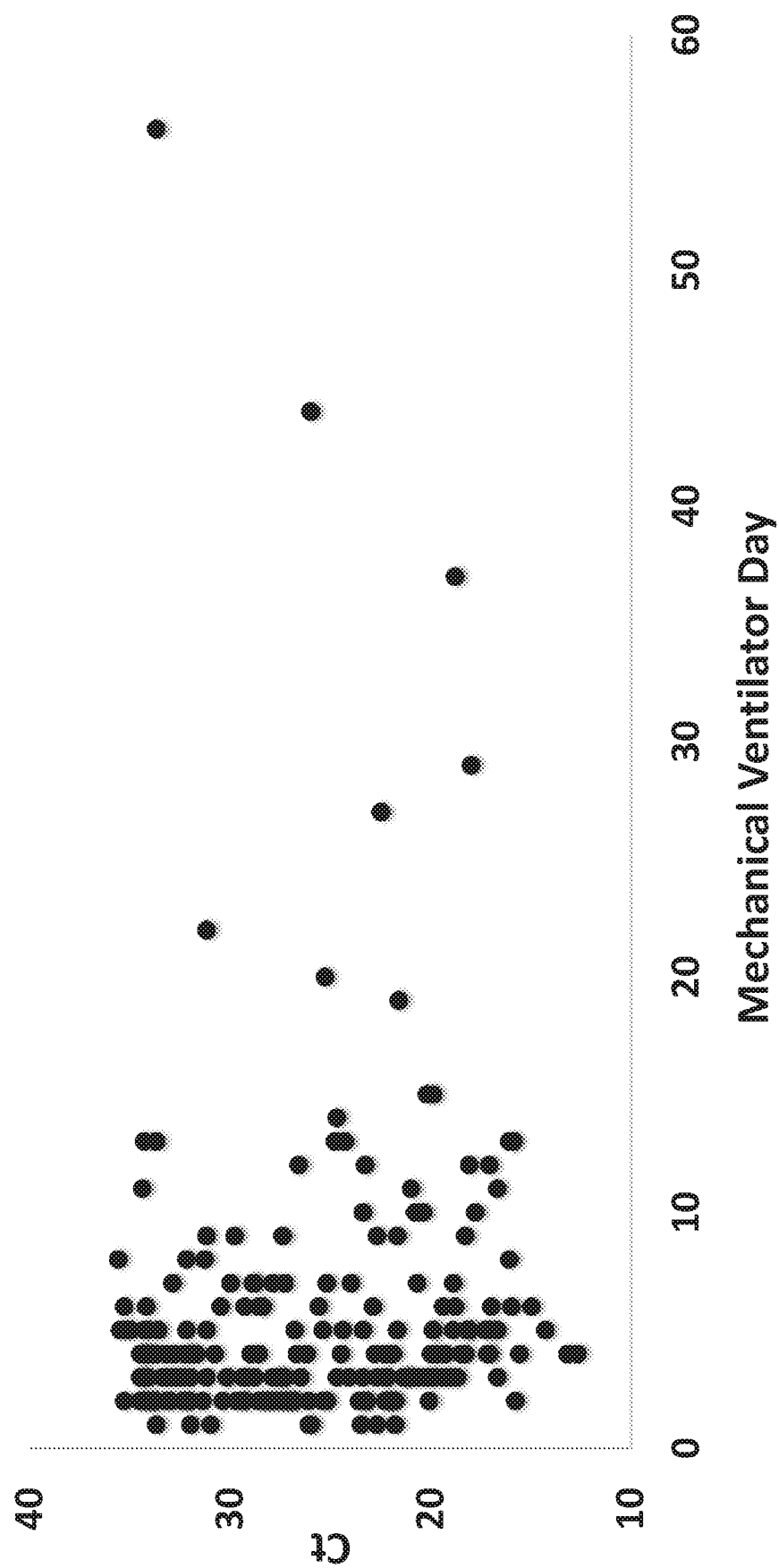
FIG. 3 is a graph showing the variability of Ct values over time on a mechanical ventilator. Even during the initial days, Ct values had a wide distribution. (See Example 2.)

The screenings occurred at various times after mechanical ventilation was initiated. Therefore, the Ct values were compared to days on mechanical ventilation. The results, shown in FIG. 3, demonstrate that Ct values had a wide distribution regardless of the number of days on mechanical ventilation. Thus, the number of days on mechanical ventilation could not be used to predict S. aureus colonization or Ct values.

EXAMPLE 3

Figure 4:
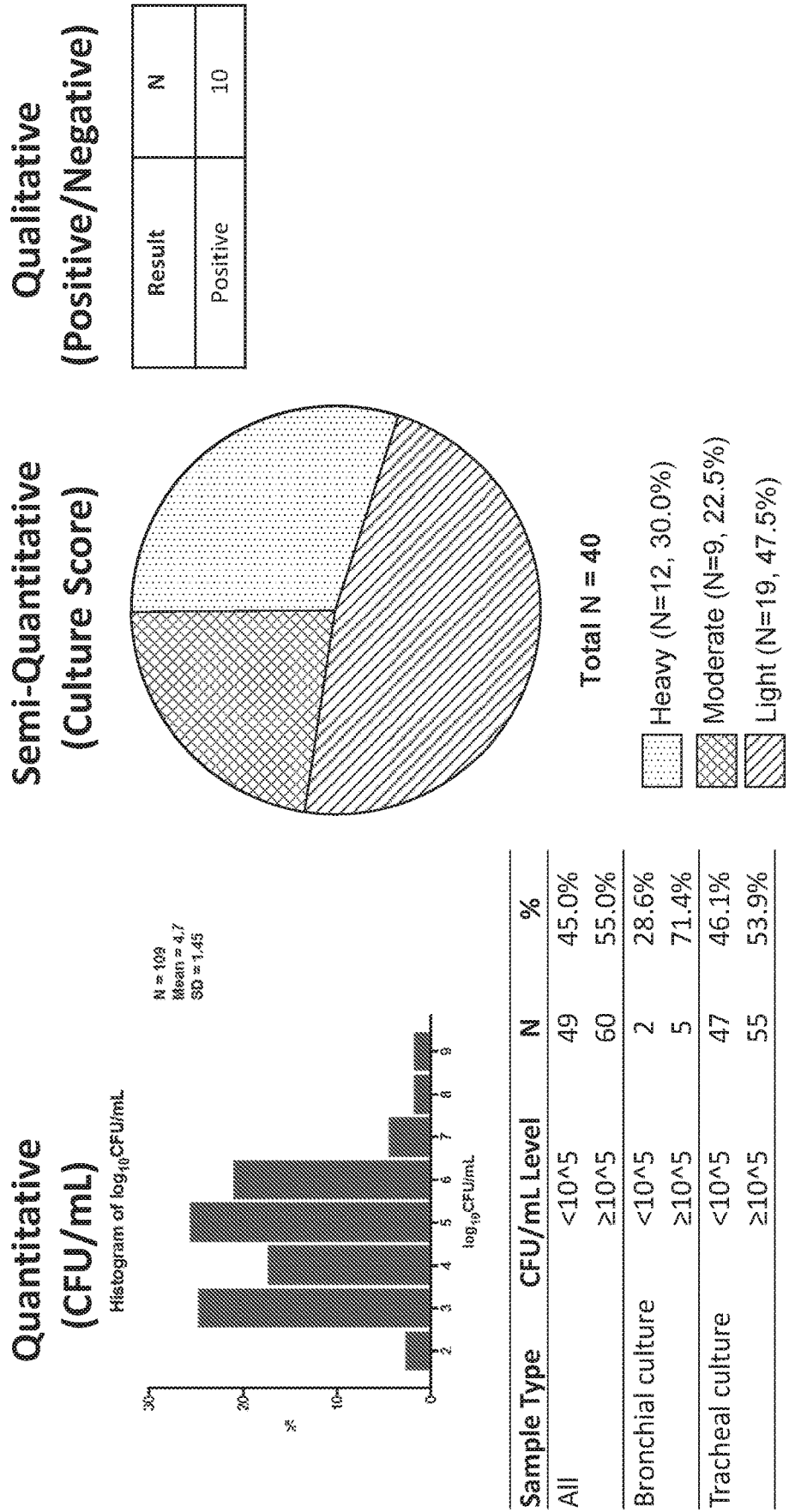
FIG. 4 shows the results from 3 different types of culture assays: a quantitative assay measuring CFU/ml, a semi-quantitative assay (culture score wherein light=+ or ++; medium=+++, and heavy=+++), and a qualitative assay (present/absent). Over half of the subjects tested had high bacterial loads (defined either by at least $10^5$ CFU/ml (in the quantitative assay) or by moderate or heavy culture sure (in the semi-quantitative assay). (See Example 3.)

This example demonstrates that rapid PCR is more sensitive that culture assays in detecting S. aureus colonization. Culture assays vary significantly between different laboratories, usually involving either plating or streaking either undiluted sample or serial dilutions of the sample on the agar containing agar plates. After incubating the plates for 24-48 hours, either the *S. aureus* scattered colonies are counted (quantitative culture method) or the number of quadrants with *S. aureus* growth and density of the growth are assessed (semi-quantitative culture method). Qualitative culture does not provide quantitation and only assesses the presence or absence of *S. aureus*. (See FIG. 4.) Thus, with different culture methods, the status of a culture (positive or negative for *S. aureus* infection) may be different and may negatively bias a treatment regimen if not accurate.

Figure 6:
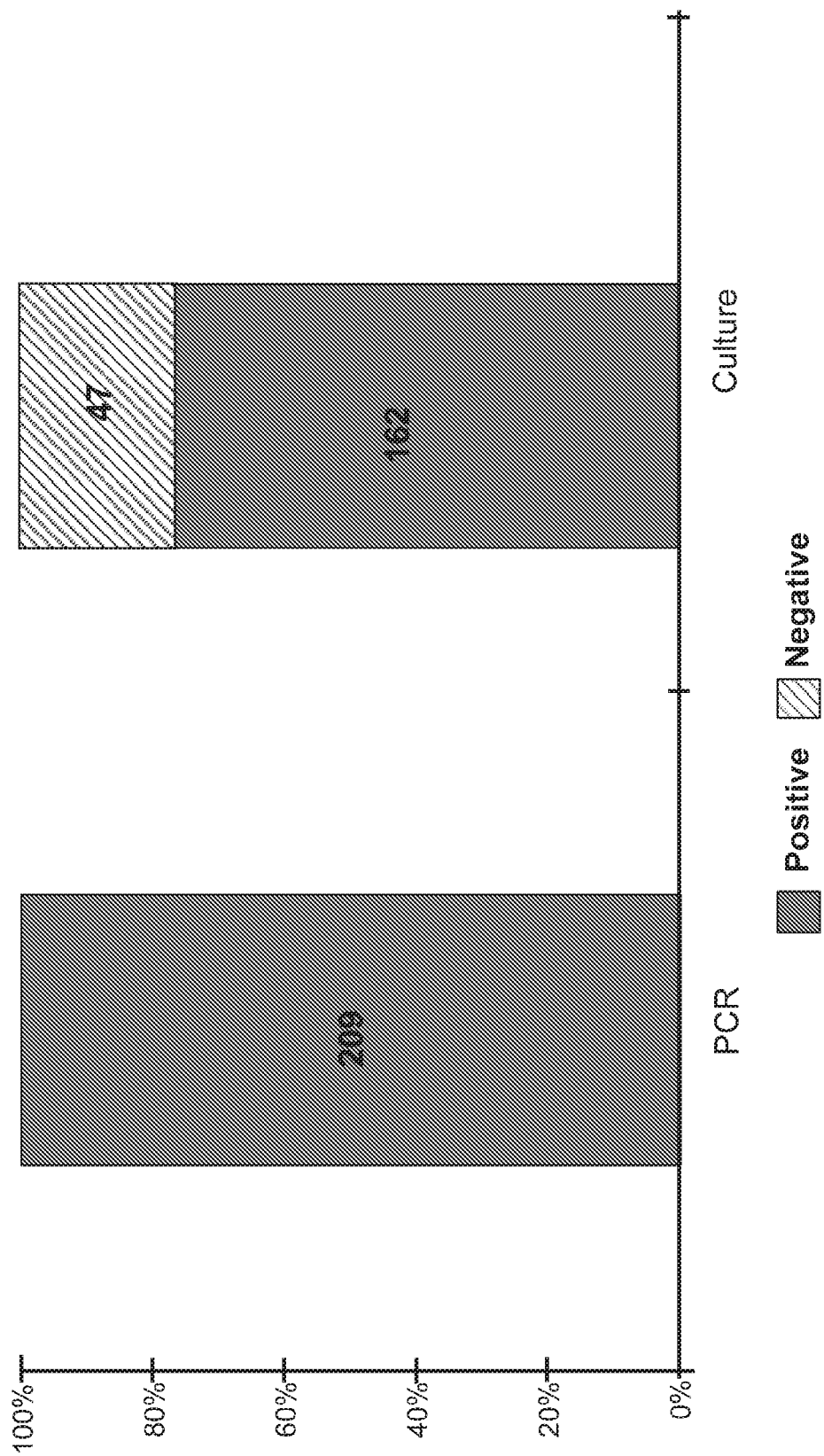
FIG. 6 provides graphs showing the concordance and discordance between PCR and culture assays for S. aureus. Out of the 209 samples that tested positive in the PCR assay, 162 also tested positive in the culture assay (77.5% concordance) while 47 of them tested negative in the culture assay (22.5% discordance). All of the discordance results from samples that tested negative in the culture assay and positive in the PCR assay. Thus, the PCR assay is more sensitive than the culture assay. (See Example 3.)

Cultures were performed on a randomized subset (N=209) of the 299 patients. Out of these 209 patients, only 162 (77.5%) produced positive culture results, whereas 47 (22.5%) produced negative culture results. Accordingly, culture assays would miss 22.5% of subjects colonized with *S. aureus*. In other words, there was a 77.5% concordance rate between the rapid PCR and culture assays, and a 22.5% discordance rate. All of the discordance was due to samples that tested positive by rapid PCR and negative by culture. (See FIG. 6.)

Figure 7:
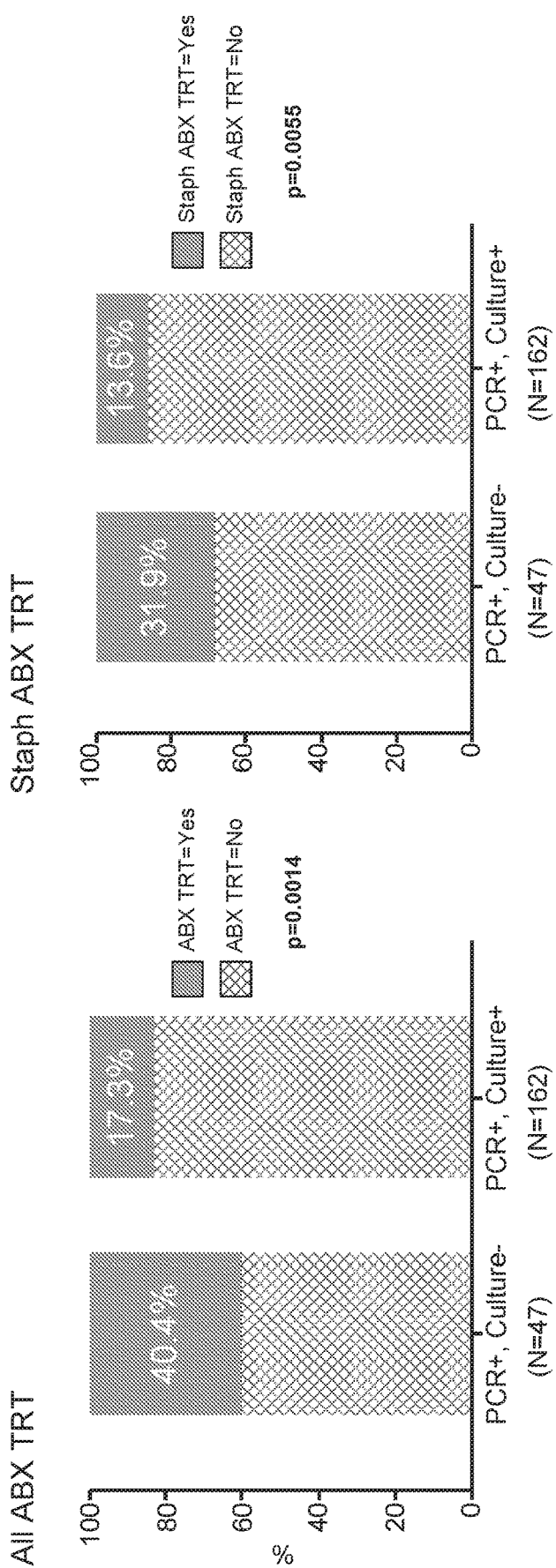
FIG. 7 provides graphs showing that antibiotic use negatively affects culture results. The percentage of patients taking antibiotics was significantly higher in the group of patients who tested positive for S. aureus by PCR, but negative for S. aureus by culture compared to the group of patients who tested positive for S. aureus by both PCR and by culture. (See Example 3.)
Figure 8:
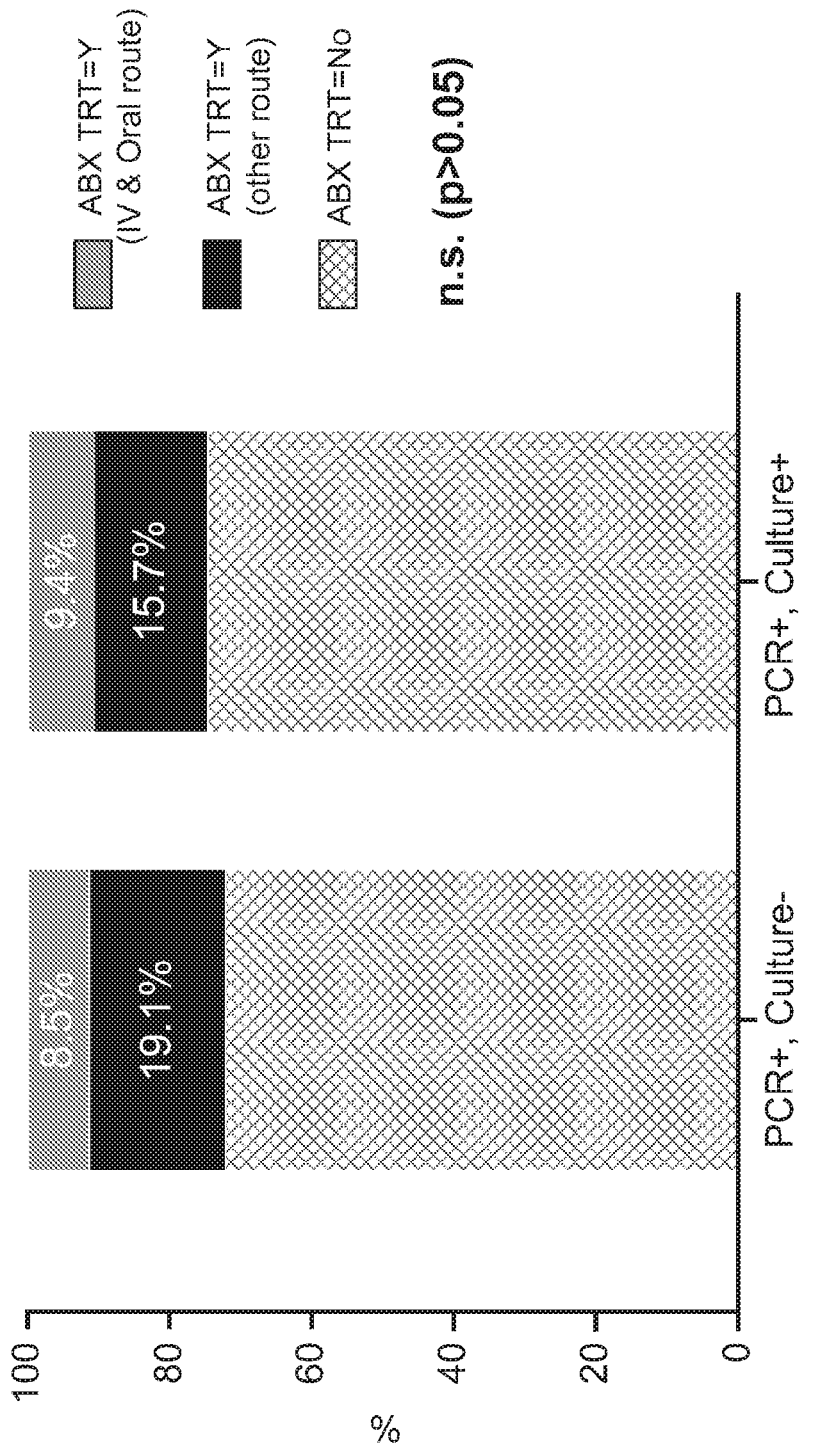
FIG. 8 provides graphs showing that historic antibiotic use had no effect on culture results. (See Example 3.)

A further review of the results demonstrated that a significantly higher percentage of patients with samples that tested positive by PCR and negative by culture were concomitantly using antibiotics than patients with samples that tested positive by PCR and by culture. (See FIG. 7.) These data suggest that antibiotic use negatively affects culture results. However, there historic antibiotic use had no effect on culture results. (See FIG. 8.)

In addition, the sensitivity of the culture assay varied in different labs due to differences in plating (e.g., sample dilution, plated volume, and number of plates). A survey of labs is summarized in the Table below.

| Lab | Limit of Detection (CFU/ml) |
|---|---|
| 1 | 100-200 |
| 2 | 100 |
| 3 | 1,000 |
| 4 | 100,000 |
| 5 | 3.3 |
| 6 | 1,000 |
| 7 | 1,000 |
| 8 | 1,000-10,000 |
| 9 | 10,000 |

Among these nine laboratories, that the limit of detection varied between 3.3 and $10^5$ CFU/ml. Thus, the low culture sensitivity in some laboratories also contributed to the discordance between the PCR and culture assays.

Figure 5:
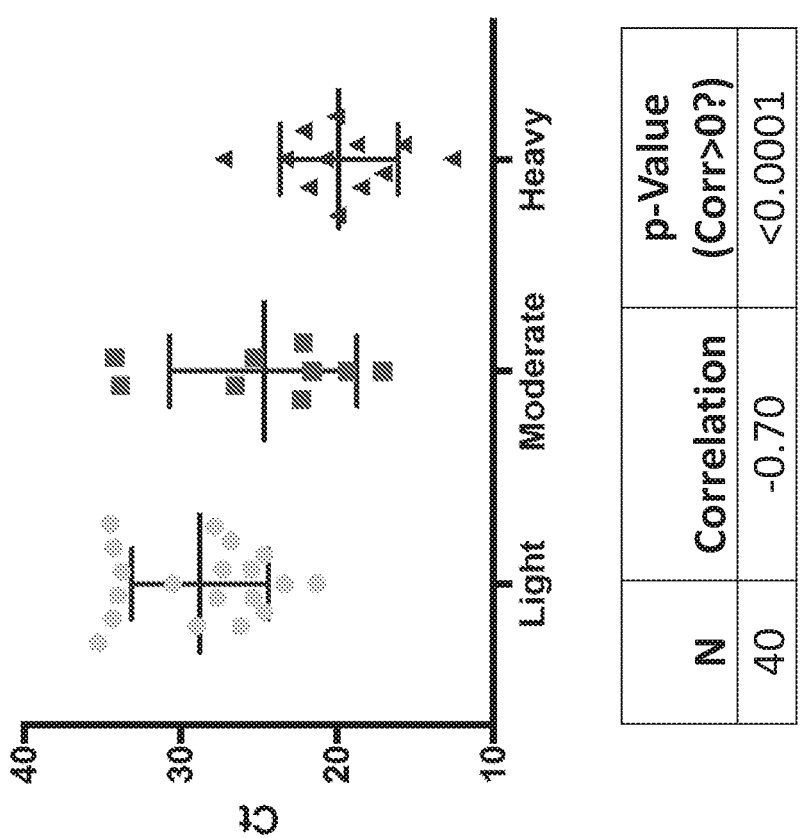
FIG. 5 provides a graph showing the Ct values obtained from samples with light, moderate, or heavy scores in the a semi-quantitative assay. (See Example 3.)

The Ct cutoff relative to whether a culture was categorized as either light, moderate, or heavy was examined. The majority of cultures categorized as heavy fell below the PCR Ct value of 29. However, a significant portion of cultures categorized as moderate also fell below the PCR Ct value of 29. Indeed, there were also some cultures categorized as light that fell below the PCR Ct value of 29. Thus, the evaluation of these cultures was inconsistent. (See FIG. 5.)

Methicillin-susceptibility determination was concordant using either the rapid PCR or the culture assay. Out of 162 samples tested by both PCR and culture, 9 (5.6%) were identified as MRSA and 153 (94.4%) were identified as MSSA regardless of the method.

These results demonstrate that culture and PCR assays are identically effective in detecting methicillin-susceptibility, but PCR assays are more sensitive in detection *S. aureus* colonization.

EXAMPLE 4

Figure 9:
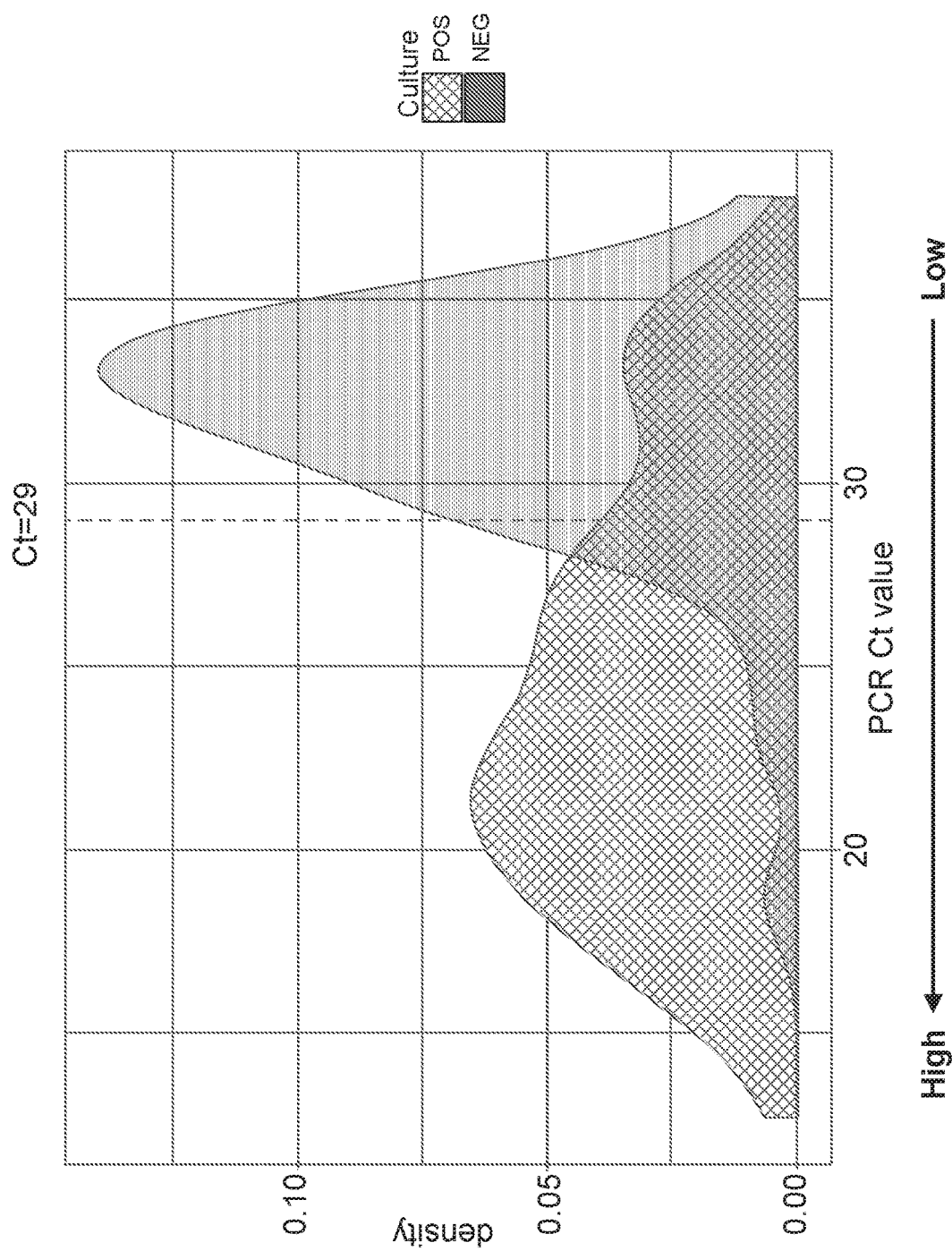
FIG. 9 provides a graph showing the distribution of culture-positive and culture-negative samples by PCR Ct value. 85% of culture-negative samples have a Ct value higher than 29 and about 80% of culture-positive samples have a Ct value lower than 29. Thus, a Ct value of 29 effectively discriminates between culture-positive and culture-negative samples. (See Example 4.)

Ct values were analyzed in culture positive and culture negative samples. The distribution of culture-positive and culture-negative samples by Ct value is shown in FIG. 9, and the results are also summarized in the table below.

|  | Ct ≤ 29 | Ct > 29 |
|---|---|---|
| Culture-negative | 14.9% | 85.1% |
| Culture-positive | 78.4% | 21.6% |

Based on these results, a Ct value of 29 does the best job of discriminating between culture-positive and culture-negative samples.

Figure 10:
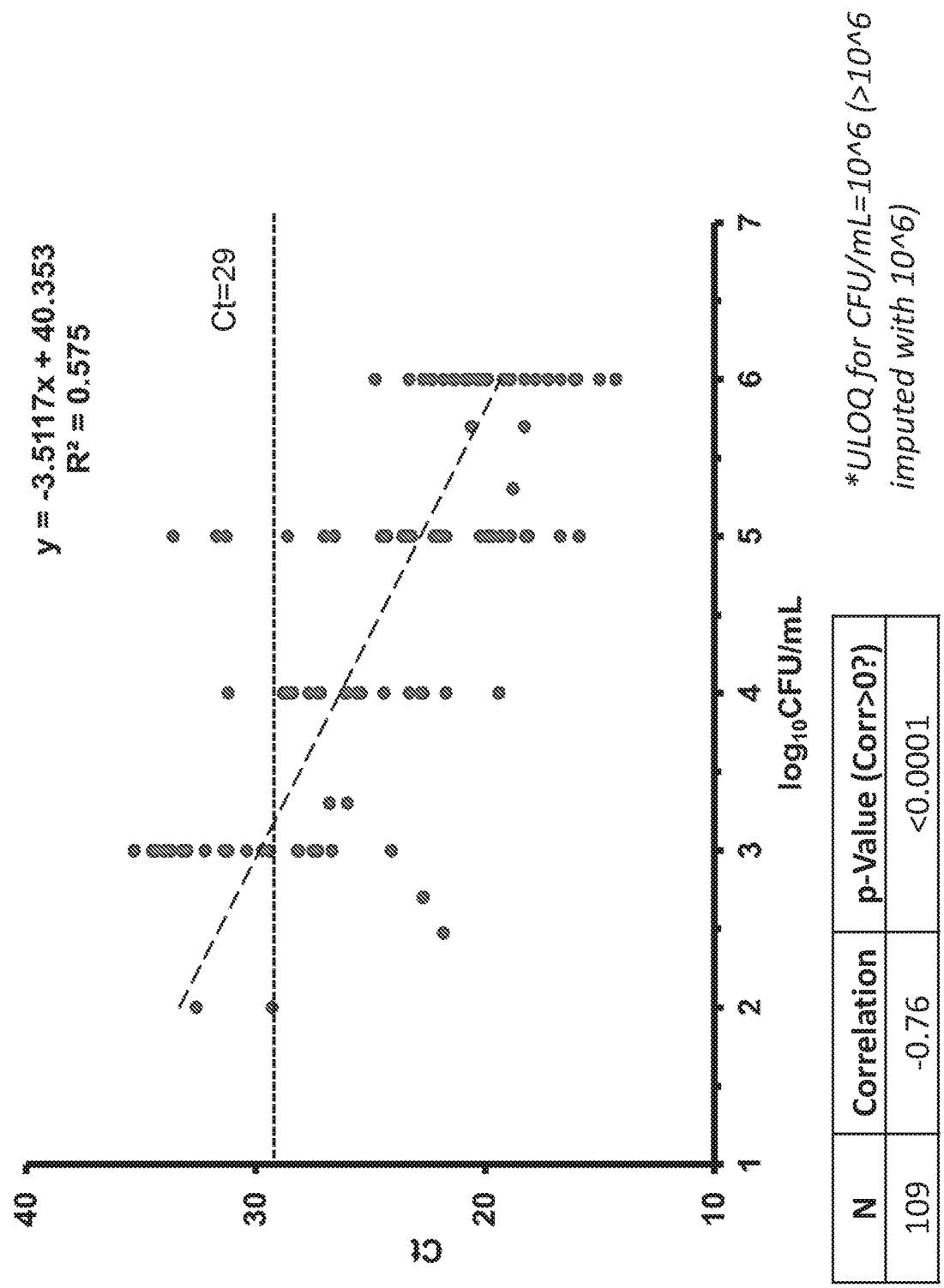
FIG. 10 provides a graph showing the relationship between Ct values and the concentration of S. aureus in a sample (colony forming units (CFU)/ml) as measured in a Phase 2 clinical trial. There was a statistically significant inverse correlation between Ct values and CFU/ml counts. Most samples with a Ct value of greater than 29 had an S. aureus load of less than or equal to $10^3$ CFU/ml. Most samples with a Ct value of less than 29 had an S. aureus load of greater than $10^3$ CFU/ml. A Ct value of 29 corresponds to about 3.2 log 10 CFU/ml (about 1600-1700 CFU/ml), and this Ct value effectively discriminates between low and high colonizers. (See Example 4.)

Ct values were also correlated with *S. aureus* concentrations. The results, shown in FIG. 10, demonstrate that there is a statistically significant inverse linear correlation between Ct values and CFU/ml counts. The majority of samples with a Ct value greater than 29 have a low *S. aureus* load ($\leq 10^3$ CFU/ml), and the majority of samples with a Ct value less than 29 had a high *S. aureus* load ($>10^4$ CFU/ml). A Ct value of 29 corresponded to about 3.2 log 10 CFU/ml (about 1600-1700 CFU/ml).

Figure 11:
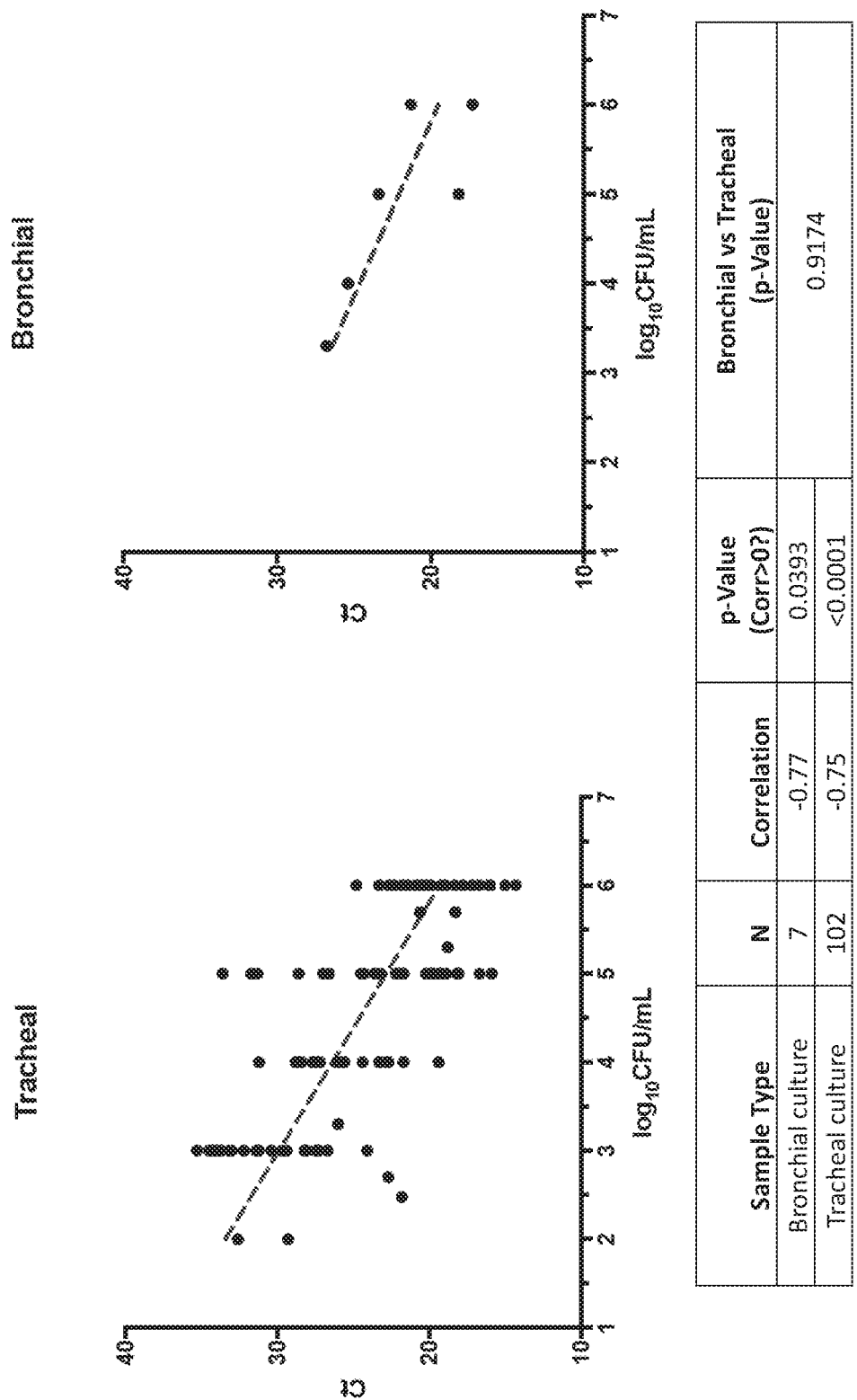
FIG. 11 provides graphs showing the relationship between Ct values and the concentration of S. aureus in a sample (colony forming units (CFU)/ml) in tracheal (left graph) and bronchial (right graph) samples. These results demonstrate that Ct values inversely correlate to S. aureus load in both tracheal and bronchial samples. (See Example 4.)

Similar correlations between Ct values and *S. aureus* concentrations were detected in bronchial cultures and tracheal cultures. (See FIG. 11.)

Figure 12:
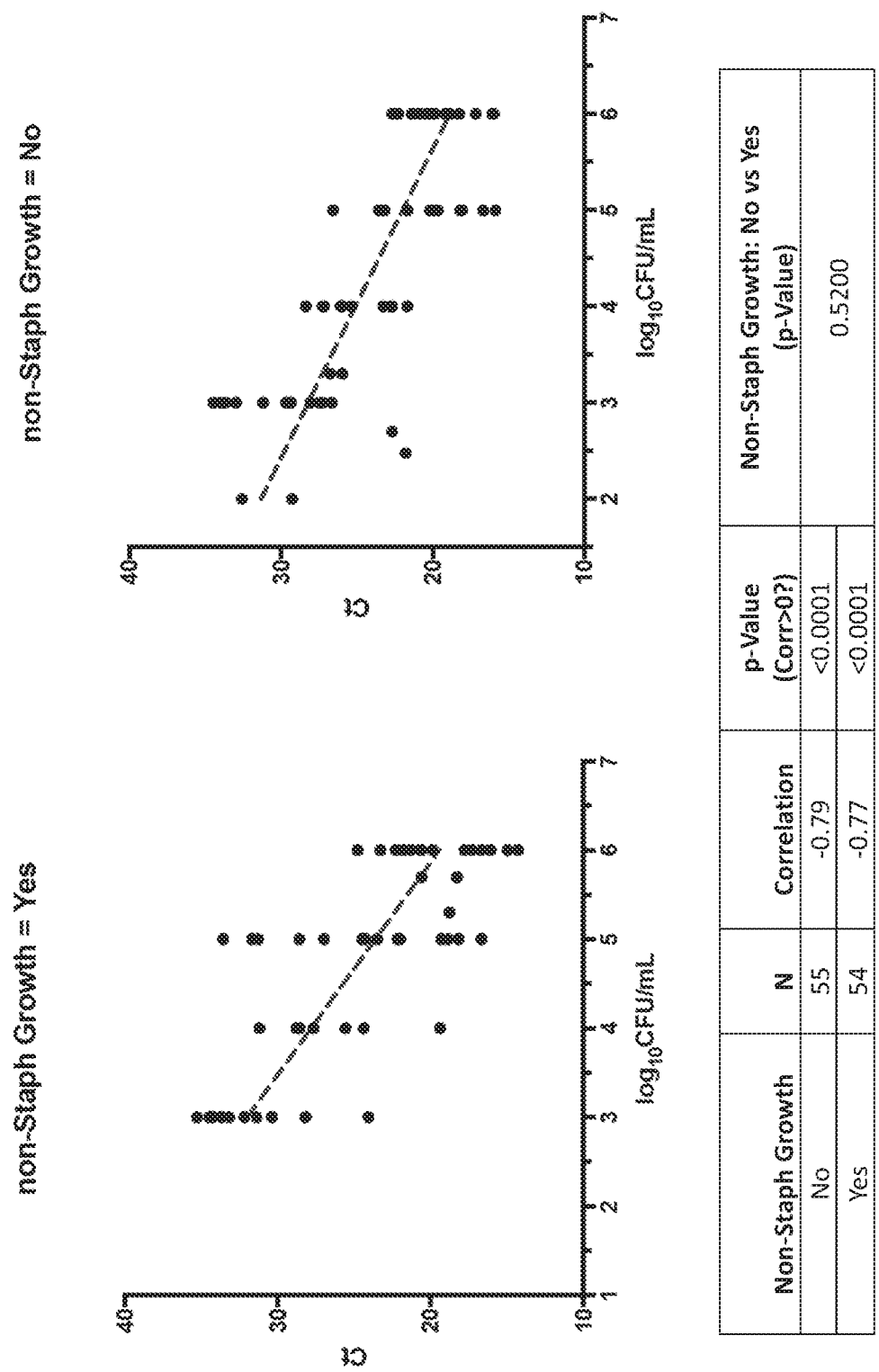
FIG. 12 provides graphs showing the relationship between Ct values and the concentration of S. aureus in a sample (colony forming units (CFU)/ml) in samples with non-Staphylococcus growth (left graph) and samples without non-Staphylococcus growth (right graph). These results show that Ct values inversely correlate to *S. aureus* load regardless of the presence or absence of non-*Staphylococcus* bacteria in a sample, which demonstrates that PCR test is specific for *S. aureus*. (See Example 4.)

Similar correlations between Ct values and *S. aureus* concentrations were also detected whether or not non-*Staphylococcus* growth was observed. (See FIG. 12)

These results demonstrate that PCR is robust way to quantify *S. aureus* colonization and that a Ct cutoff of 29 effectively discriminates between low and high *S. aureus* colonization.

EXAMPLE 5

The efficacy of the anti-*S. aureus* antibody MEDI4893 in preventing *S. aureus* pneumonia in mechanically ventilated ICU patients was compared in patients with low and high levels of *S. aureus* colonization using a Ct cutoff value of 29.

Subjects were considered mechanically ventilated when they (i) were intubated with an endotracheal or nasotracheal tube and receiving positive pressure ventilation support or (ii) were not intubated with an endotracheal or nasotracheal tube, but required at least 8 hours of positive pressure ventilation (e.g., patients with tracheostomy, continuous positive airway pressure [CPAP], etc.) within the past 24 hours).

*S. aureus* pneumonia was diagnosed in patients who were mechanically ventilated at the time of diagnosis when they met the following radiographic, clinical, and microbiological criteria that were not due to any overt non-infectious causes.

Radiographic criteria: new or worsening infiltrate consistent with pneumonia on chest X-ray obtained within 24 hours of the event (diagnosed by a qualified radiologist); and Clinical criteria: at least 2 of the following minor or 1 major respiratory signs or symptoms of new onset Minor criteria Systemic signs of infection (one or more of the following): Abnormal temperature (oral or tympanic temperature>38° C. or a core temperature≥38.3° C. or hypothermia, defined as a core body temperature of <35° C.), and/or abnormal white blood cell (WBC) (WBC count>10,000 cells/mm3, WBC count<4500 cells/mm3, or >15% band neutrophils);
Production of purulent endotracheal secretions
Physical examination findings consistent with pneumonia/pulmonary consolidation (e.g., rales, rhonchi, bronchial breath sounds), dullness to percussion
Major criteria
Acute changes made in the ventilatory support system to enhance oxygenation, as determined by:
$PaO_2/FiO_2$ ratio<240 mmHg maintained for at least 4 hours, or
A decrease in $PaO_2/FiO_2$ by ≥50 mmHg maintained for at least 4 hours and
Microbiological confirmation: at least 1 of the following (obtained within 24 hours of the onset of the event)
Respiratory specimen is positive for S. aureus by culture. Includes a specimen of respiratory secretions obtained by endotracheal aspiration or by bronchoscopy with bronchoalveolar lavage (BAL) or protected-specimen brush (PSB) sampling in intubated subjects. In subjects who are not intubated but meet the protocol definition of mechanical ventilation, a specimen of expectorated sputum was acceptable
Blood culture positive for S. aureus (and no apparent primary source of infection outside of the lung)
Pleural fluid aspirate or lung tissue culture positive for S. aureus during episode of pneumonia
The results are shown in the Tables below.

| Placebo (N = 100) | MEDI4893 5000 mg (N = 96) | Relative Risk Reduction | 90% CI | p-value |
|---|---|---|---|---|
| 26 (26.0%) | 17 (17.7%) | 31.9% | (−7.5%, 56.8) | 0.166 |

Relative risk reduction (MEDI4893 5000 mg versus placebo; 90% confidence interval (CI), and p-value based on Poisson regression with robust variance.
An 82.6% relative risk reduction (90% CI: −1.0%, 97.0%;) of S. aureus-only pneumonia, a 30.6% relative risk reduction (90% CI: −4.9%, 54.0%) of all cause pneumonia and a 23.1% relative risk reduction (90% CI: 23.1%−4.9%, 43.6%) of all cause pneumonia or death were also observed.

| Subgroup | Interaction p-value | Placebo (N = 100) | MEDI4893 5000 mg (N = 96) | Relative Risk Reduction | 90% CI |
|---|---|---|---|---|---|
| SPA CT Value ≥ 29 "Low" | 0.069 | 12/36 (33.3%) | 4/36 (11.1%) | 66.7% | (21.3%, 86.2%) |
| SPA CT Value < 29 "High" | | 14/63 (22.2%) | 13/60 (21.7%) | 2.5% | (−70.4%, 45.3%) |

The interaction p-value is obtained from Poisson regression with robust variance, including the terms of treatment group, subgroup being tested, and treatment by subgroup interaction. The relative risk reduction (MEDI4893 5000 mg versus placebo) and 90% confidence interval (CI) were based on unconditional confidence interval on ratio of proportions.
Patients with a Ct value of at least 29 (low S. aureus) had a 33.3% attack rate and MEDI4893 produced a statistically significant relative reduction of risk (RRR) of about 67%. In contrast, the overall population had a 26% attack rate and MEDI4893 produced a RRR of 32% that was not statistically significant. Those with a Ct value of less than 29 (high S. aureus) had a 22.2% attack rate, and a RRR of about 2.5% that was not statistically significant.

These results demonstrate that immunoprophylaxis with the anti-alpha toxin antibody MEDI4893 showed increased efficacy in patients with low S. aureus colonization.

EXAMPLE 6

The effect of the anti-S. aureus antibody MEDI4893 on health resource utilization savings was also analyzed. Key results are summarized in the table below.

| | Patients ≤ 65 years of Age | | |
|---|---|---|---|
| Health Resource Utilization | Placebo N = 69 | MEDI4893 N = 59 | Days Saved/Pt |
| Mean Hospitalization duration (days) | 39.1 | 30.3 | 8.8 |
| Hospitalization duration Adjusted for 90 Days Study Follow-up | 45.7 | 35.6 | 10.1 |
| Mean Hospital-Free days | 37.7 | 46.2 | 8.5 |
| Mean ICU (days) | 20.0 | 16.7 | 3.3 |
| ICU duration Adjusted for 90 Days Study Follow-up | 23.4 | 19.7 | 3.7 |
| Mean ICU-Free days | 55.9 | 58.5 | 2.6 |
| Mean Mechanical Ventilation (MV) duration (days) | 1.1 | 14.6 | 12.7 |
| MV duration Adjusted for 90 Days Study Follow-up | 1.2 | 17.1 | 14.9 |
| Mean MV-Free days | −0.2 | 60.9 | 62.1 |

These results demonstrate that MEDI4893 decreased the duration of hospital stays, the duration of ICU stays, and the duration of mechanical ventilation.

All references, including publications, patent applications, and patents, cited herein are hereby incorporated by reference to the same extent as if each reference were individually and specifically indicated to be incorporated by reference and were set forth in its entirety herein.

Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A method of treating a subject colonized with *Staphylococcus aureus* (*S. aureus*), the method comprising administering an antibody or antigen-binding fragment thereof that binds to *S. aureus* alpha toxin (AT) to the subject, wherein polymerase chain reaction (PCR) has been used to detect the level of *S. aureus* in a sample that was obtained from the subject prior to the administering, wherein the sample has a level of *S. aureus* that does not exceed a level of *S. aureus* that correlates to a polymerase chain reaction (PCR) cycle threshold (Ct) value of 29 or above, wherein the PCR Ct value of 29 corresponds to a sample concentration of *S. aureus* that does not exceed 1700 colony forming units (CFU)/mL of *S. aureus*, and wherein the antibody or antigen-binding fragment thereof that binds to *S. aureus* AT comprises a variable heavy chain (VH) complementarity determining region (CDR) 1 comprising the amino acid sequence of SEQ ID NO: 1, a VH CDR2 comprising the amino acid sequence of SEQ ID NO:2, a VH CDR3 comprising the amino acid sequence of SEQ ID NO:3, a variable light chain (VL) CDR1 comprising the amino acid sequence of SEQ ID NO:4, a VL CDR2 comprising the amino acid sequence of SEQ ID NO:5, and a VL CDR3 comprising the amino acid sequence of SEQ ID NO:6.

2. The method of claim 1, wherein the antibody or antigen-binding fragment thereof that binds to *S. aureus* AT comprises a VH comprising the amino acid sequence of SEQ ID NO:7 and a VL comprising the amino acid sequence of SEQ ID NO:8.

3. The method of claim 1, wherein the subject has *S. aureus* pneumonia.

4. The method of claim 1, wherein the PCR detects *S. aureus* protein A.

5. The method of claim 1, wherein the subject is taking antibiotics.

6. The method of claim 1, wherein the sample was obtained from the lower respiratory tract of the subject.

7. The method of claim 1, wherein the sample contains bacteria that would not grow in a culture to identify *S. aureus*.

8. The method of claim 1, wherein the *S. aureus* is antibiotic resistant.

9. The method of claim 1, further comprising determining whether the *S. aureus* is methicillin-resistant.

10. The method of claim 1, wherein the antibody or antigen binding fragment thereof that binds to *S. aureus* AT comprises a Fc region with a M252Y, S254T, and T256E (YTE) mutation.

11. The method of claim 1, wherein the antibody or antigen-binding fragment that binds to *S. aureus* AT is a monoclonal antibody or antigen-binding fragment.

12. The method of claim 1, wherein the antibody or antigen-binding fragment thereof comprises a heavy chain amino acid sequence of SEQ ID NO:11 and a light chain amino acid sequence of SEQ ID NO: 10.

13. The method of claim 3, wherein the antibody or antigen-binding fragment thereof comprises a heavy chain amino acid sequence of SEQ ID NO:11 and a light chain amino acid sequence of SEQ ID NO:10.

14. The method of claim 2, wherein the antibody or antigen binding fragment thereof that binds to *S. aureus* AT comprises a Fc region with a M252Y, S254T, and T256E (YTE) mutation.

15. The method of claim 2, wherein the antibody or antigen-binding fragment that binds to *S. aureus* AT is a monoclonal antibody or antigen-binding fragment.

16. The method of claim 2, wherein the PCR detects *S. aureus* protein A.

17. The method of claim 2, wherein the subject is taking antibiotics.

18. The method of claim 2, wherein the sample was obtained from the lower respiratory tract of the subject.

19. The method of claim 2, wherein the sample contains bacteria that would not grow in a culture to identify *S. aureus*.

20. The method of claim 2, wherein the *S. aureus* is antibiotic resistant.

* * * * *

```
                              SEQUENCE LISTING

<160> NUMBER OF SEQ ID NOS: 13

<210> SEQ ID NO 1
<211> LENGTH: 5
<212> TYPE: PRT
<213> ORGANISM: Artificial Sequence
<220> FEATURE:
<223> OTHER INFORMATION: VH CDR1 MEDI4893

<400> SEQUENCE: 1

Ser His Asp Met His
1               5

<210> SEQ ID NO 2
<211> LENGTH: 16
<212> TYPE: PRT
<213> ORGANISM: Artificial Sequence
<220> FEATURE:
<223> OTHER INFORMATION: VH CDR2 MEDI4893

<400> SEQUENCE: 2

Gly Ile Gly Thr Ala Gly Asp Thr Tyr Tyr Pro Asp Ser Val Lys Gly
1               5                   10                  15

<210> SEQ ID NO 3
<211> LENGTH: 14
<212> TYPE: PRT
<213> ORGANISM: Artificial Sequence
<220> FEATURE:
<223> OTHER INFORMATION: VH CDR3 MEDI4893

<400> SEQUENCE: 3

Asp Arg Tyr Ser Pro Thr Gly His Tyr Tyr Gly Met Asp Val
1               5                   10

<210> SEQ ID NO 4
<211> LENGTH: 11
<212> TYPE: PRT
<213> ORGANISM: Artificial Sequence
<220> FEATURE:
<223> OTHER INFORMATION: VL CDR1 MEDI4893

<400> SEQUENCE: 4

Arg Ala Ser Gln Ser Ile Ser Ser Trp Leu Ala
1               5                   10

<210> SEQ ID NO 5
<211> LENGTH: 7
<212> TYPE: PRT
<213> ORGANISM: Artificial Sequence
<220> FEATURE:
<223> OTHER INFORMATION: VL CDR2 MEDI4893

<400> SEQUENCE: 5

Lys Ala Ser Ser Leu Glu Ser
1               5

<210> SEQ ID NO 6
<211> LENGTH: 8
<212> TYPE: PRT
<213> ORGANISM: Artificial Sequence
```

```
<220> FEATURE:
<223> OTHER INFORMATION: VL CDR3 MEDI4893

<400> SEQUENCE: 6

Lys Gln Tyr Ala Asp Tyr Trp Thr
1               5

<210> SEQ ID NO 7
<211> LENGTH: 122
<212> TYPE: PRT
<213> ORGANISM: Artificial Sequence
<220> FEATURE:
<223> OTHER INFORMATION: Variable Heavy Chain  MEDI4893

<400> SEQUENCE: 7

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser His
            20                  25                  30

Asp Met His Trp Val Arg Gln Ala Thr Gly Lys Gly Leu Glu Trp Val
        35                  40                  45

Ser Gly Ile Gly Thr Ala Gly Asp Thr Tyr Tyr Pro Asp Ser Val Lys
    50                  55                  60

Gly Arg Phe Thr Ile Ser Arg Glu Asn Ala Lys Asn Ser Leu Tyr Leu
65                  70                  75                  80

Gln Met Asn Ser Leu Arg Ala Gly Asp Thr Ala Val Tyr Tyr Cys Ala
                85                  90                  95

Arg Asp Arg Tyr Ser Pro Thr Gly His Tyr Tyr Gly Met Asp Val Trp
            100                 105                 110

Gly Gln Gly Thr Thr Val Thr Val Ser Ser
        115                 120

<210> SEQ ID NO 8
<211> LENGTH: 106
<212> TYPE: PRT
<213> ORGANISM: Artificial Sequence
<220> FEATURE:
<223> OTHER INFORMATION: Variable Light Chain MEDI4893

<400> SEQUENCE: 8

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
        35                  40                  45

Tyr Lys Ala Ser Ser Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Lys Gln Tyr Ala Asp Tyr Trp Thr
                85                  90                  95

Phe Gly Gln Gly Thr Lys Val Glu Ile Lys
            100                 105

<210> SEQ ID NO 9
<211> LENGTH: 452
<212> TYPE: PRT
<213> ORGANISM: Artificial Sequence
<220> FEATURE:
```

<223> OTHER INFORMATION: Full-Length Heavy Chain MEDI4893

<400> SEQUENCE: 9

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser His
            20                  25                  30

Asp Met His Trp Val Arg Gln Ala Thr Gly Lys Gly Leu Glu Trp Val
        35                  40                  45

Ser Gly Ile Gly Thr Ala Gly Asp Thr Tyr Tyr Pro Asp Ser Val Lys
    50                  55                  60

Gly Arg Phe Thr Ile Ser Arg Glu Asn Ala Lys Asn Ser Leu Tyr Leu
65                  70                  75                  80

Gln Met Asn Ser Leu Arg Ala Gly Asp Thr Ala Val Tyr Tyr Cys Ala
            85                  90                  95

Arg Asp Arg Tyr Ser Pro Thr Gly His Tyr Tyr Gly Met Asp Val Trp
        100                 105                 110

Gly Gln Gly Thr Thr Val Thr Val Ser Ser Ala Ser Thr Lys Gly Pro
    115                 120                 125

Ser Val Phe Pro Leu Ala Pro Ser Ser Lys Ser Thr Ser Gly Gly Thr
130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
            165                 170                 175

Ala Val Leu Gln Ser Ser Gly Leu Tyr Ser Leu Ser Ser Val Val Thr
        180                 185                 190

Val Pro Ser Ser Ser Leu Gly Thr Gln Thr Tyr Ile Cys Asn Val Asn
    195                 200                 205

His Lys Pro Ser Asn Thr Lys Val Asp Lys Arg Val Glu Pro Lys Ser
210                 215                 220

Cys Asp Lys Thr His Thr Cys Pro Pro Cys Pro Ala Pro Glu Leu Leu
225                 230                 235                 240

Gly Gly Pro Ser Val Phe Leu Phe Pro Pro Lys Pro Lys Asp Thr Leu
            245                 250                 255

Tyr Ile Thr Arg Glu Pro Glu Val Thr Cys Val Val Val Asp Val Ser
        260                 265                 270

His Glu Asp Pro Glu Val Lys Phe Asn Trp Tyr Val Asp Gly Val Glu
    275                 280                 285

Val His Asn Ala Lys Thr Lys Pro Arg Glu Glu Gln Tyr Asn Ser Thr
290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Pro Ala Pro
            325                 330                 335

Ile Glu Lys Thr Ile Ser Lys Ala Lys Gly Gln Pro Arg Glu Pro Gln
        340                 345                 350

Val Tyr Thr Leu Pro Pro Ser Arg Glu Glu Met Thr Lys Asn Gln Val
    355                 360                 365

Ser Leu Thr Cys Leu Val Lys Gly Phe Tyr Pro Ser Asp Ile Ala Val
370                 375                 380

Glu Trp Glu Ser Asn Gly Gln Pro Glu Asn Asn Tyr Lys Thr Thr Pro
385                 390                 395                 400

```
Pro Val Leu Asp Ser Asp Gly Ser Phe Phe Leu Tyr Ser Lys Leu Thr
            405                 410                 415

Val Asp Lys Ser Arg Trp Gln Gln Gly Asn Val Phe Ser Cys Ser Val
            420                 425                 430

Met His Glu Ala Leu His Asn His Tyr Thr Gln Lys Ser Leu Ser Leu
            435                 440                 445

Ser Pro Gly Lys
    450

<210> SEQ ID NO 10
<211> LENGTH: 212
<212> TYPE: PRT
<213> ORGANISM: Artificial Sequence
<220> FEATURE:
<223> OTHER INFORMATION: Full-length light chain MEDI4893*

<400> SEQUENCE: 10

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
        35                  40                  45

Tyr Lys Ala Ser Ser Leu Glu Ser Gly Val Pro Ser Arg Phe Ser Gly
50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Lys Gln Tyr Ala Asp Tyr Trp Thr
                85                  90                  95

Phe Gly Gln Gly Thr Lys Val Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu
    210

<210> SEQ ID NO 11
<211> LENGTH: 452
<212> TYPE: PRT
<213> ORGANISM: Artificial Sequence
<220> FEATURE:
<223> OTHER INFORMATION: Full-Length Heavy Chain MEDI4893*

<400> SEQUENCE: 11

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser His
            20                  25                  30
```

```
Asp Met His Trp Val Arg Gln Ala Thr Gly Lys Gly Leu Glu Trp Val
         35                  40                  45
Ser Gly Ile Gly Thr Ala Gly Asp Thr Tyr Tyr Pro Asp Ser Val Lys
 50                  55                  60
Gly Arg Phe Thr Ile Ser Arg Glu Asn Ala Lys Asn Ser Leu Tyr Leu
 65                  70                  75                  80
Gln Met Asn Ser Leu Arg Ala Gly Asp Thr Ala Val Tyr Tyr Cys Ala
                 85                  90                  95
Arg Asp Arg Tyr Ser Pro Thr Gly His Tyr Tyr Gly Met Asp Val Trp
             100                 105                 110
Gly Gln Gly Thr Thr Val Thr Val Ser Ser Ala Ser Thr Lys Gly Pro
             115                 120                 125
Ser Val Phe Pro Leu Ala Pro Ser Ser Lys Ser Thr Ser Gly Gly Thr
         130                 135                 140
Ala Ala Leu Gly Cys Leu Val Lys Asp Tyr Phe Pro Glu Pro Val Thr
145                 150                 155                 160
Val Ser Trp Asn Ser Gly Ala Leu Thr Ser Gly Val His Thr Phe Pro
                 165                 170                 175
Ala Val Leu Gln Ser Ser Gly Leu Tyr Ser Leu Ser Ser Val Val Thr
             180                 185                 190
Val Pro Ser Ser Ser Leu Gly Thr Gln Thr Tyr Ile Cys Asn Val Asn
         195                 200                 205
His Lys Pro Ser Asn Thr Lys Val Asp Lys Arg Val Glu Pro Lys Ser
         210                 215                 220
Cys Asp Lys Thr His Thr Cys Pro Pro Cys Pro Ala Pro Glu Leu Leu
225                 230                 235                 240
Gly Gly Pro Ser Val Phe Leu Phe Pro Pro Lys Pro Lys Asp Thr Leu
                 245                 250                 255
Met Ile Ser Arg Thr Pro Glu Val Thr Cys Val Val Val Asp Val Ser
             260                 265                 270
His Glu Asp Pro Glu Val Lys Phe Asn Trp Tyr Val Asp Gly Val Glu
         275                 280                 285
Val His Asn Ala Lys Thr Lys Pro Arg Glu Glu Gln Tyr Asn Ser Thr
         290                 295                 300
Tyr Arg Val Val Ser Val Leu Thr Val Leu His Gln Asp Trp Leu Asn
305                 310                 315                 320
Gly Lys Glu Tyr Lys Cys Lys Val Ser Asn Lys Ala Leu Pro Ala Pro
                 325                 330                 335
Ile Glu Lys Thr Ile Ser Lys Ala Lys Gly Gln Pro Arg Glu Pro Gln
             340                 345                 350
Val Tyr Thr Leu Pro Pro Ser Arg Glu Glu Met Thr Lys Asn Gln Val
         355                 360                 365
Ser Leu Thr Cys Leu Val Lys Gly Phe Tyr Pro Ser Asp Ile Ala Val
         370                 375                 380
Glu Trp Glu Ser Asn Gly Gln Pro Glu Asn Asn Tyr Lys Thr Thr Pro
385                 390                 395                 400
Pro Val Leu Asp Ser Asp Gly Ser Phe Phe Leu Tyr Ser Lys Leu Thr
                 405                 410                 415
Val Asp Lys Ser Arg Trp Gln Gln Gly Asn Val Phe Ser Cys Ser Val
             420                 425                 430
Met His Glu Ala Leu His Asn His Tyr Thr Gln Lys Ser Leu Ser Leu
         435                 440                 445
```

```
Ser Pro Gly Lys
    450
```

<210> SEQ ID NO 12
<211> LENGTH: 293
<212> TYPE: PRT
<213> ORGANISM: Staphylococcus aureus

<400> SEQUENCE: 12

```
Ala Asp Ser Asp Ile Asn Ile Lys Thr Gly Thr Thr Asp Ile Gly Ser
1               5                   10                  15

Asn Thr Thr Val Lys Thr Gly Asp Leu Val Thr Tyr Asp Lys Glu Asn
                20                  25                  30

Gly Met His Lys Lys Val Phe Tyr Ser Phe Ile Asp Asp Lys Asn His
            35                  40                  45

Asn Lys Lys Leu Leu Val Ile Arg Thr Lys Gly Thr Ile Ala Gly Gln
    50                  55                  60

Tyr Arg Val Tyr Ser Glu Glu Gly Ala Asn Lys Ser Gly Leu Ala Trp
65                  70                  75                  80

Pro Ser Ala Phe Lys Val Gln Leu Gln Leu Pro Asp Asn Glu Val Ala
                85                  90                  95

Gln Ile Ser Asp Tyr Tyr Pro Arg Asn Ser Ile Asp Thr Lys Glu Tyr
            100                 105                 110

Met Ser Thr Leu Thr Tyr Gly Phe Asn Gly Asn Val Thr Gly Asp Asp
        115                 120                 125

Thr Gly Lys Ile Gly Gly Leu Ile Gly Ala Asn Val Ser Ile Gly His
    130                 135                 140

Thr Leu Lys Tyr Val Gln Pro Asp Phe Lys Thr Ile Leu Glu Ser Pro
145                 150                 155                 160

Thr Asp Lys Lys Val Gly Trp Lys Val Ile Phe Asn Asn Met Val Asn
                165                 170                 175

Gln Asn Trp Gly Pro Tyr Asp Arg Asp Ser Trp Asn Pro Val Tyr Gly
            180                 185                 190

Asn Gln Leu Phe Met Lys Thr Arg Asn Gly Ser Met Lys Ala Ala Asp
        195                 200                 205

Asn Phe Leu Asp Pro Asn Lys Ala Ser Ser Leu Leu Ser Ser Gly Phe
    210                 215                 220

Ser Pro Asp Phe Ala Thr Val Ile Thr Met Asp Arg Lys Ala Ser Lys
225                 230                 235                 240

Gln Gln Thr Asn Ile Asp Val Ile Tyr Glu Arg Val Arg Asp Asp Tyr
                245                 250                 255

Gln Leu His Trp Thr Ser Thr Asn Trp Lys Gly Thr Asn Thr Lys Asp
            260                 265                 270

Lys Trp Thr Asp Arg Ser Ser Glu Arg Tyr Lys Ile Asp Trp Glu Lys
        275                 280                 285

Glu Glu Met Thr Asn
    290
```

<210> SEQ ID NO 13
<211> LENGTH: 292
<212> TYPE: PRT
<213> ORGANISM: Staphylococcus aureus

<400> SEQUENCE: 13

```
Asp Ser Asp Ile Asn Ile Lys Thr Gly Thr Thr Asp Ile Gly Ser Asn
1               5                   10                  15
```

-continued

```
Thr Thr Val Lys Thr Gly Asp Leu Val Thr Tyr Asp Lys Glu Asn Gly
            20              25              30

Met Leu Lys Lys Val Phe Tyr Ser Phe Ile Asp Lys Asn His Asn
        35              40              45

Lys Lys Leu Leu Val Ile Arg Thr Lys Gly Thr Ile Ala Gly Gln Tyr
        50              55              60

Arg Val Tyr Ser Glu Glu Gly Ala Asn Lys Ser Gly Leu Ala Trp Pro
65              70              75              80

Ser Ala Phe Lys Val Gln Leu Gln Leu Pro Asp Asn Glu Val Ala Gln
            85              90              95

Ile Ser Asp Tyr Tyr Pro Arg Asn Ser Ile Asp Thr Lys Glu Tyr Met
            100             105             110

Ser Thr Leu Thr Tyr Gly Phe Asn Gly Asn Val Thr Gly Asp Asp Thr
            115             120             125

Gly Lys Ile Gly Gly Leu Ile Gly Ala Asn Val Ser Ile Gly His Thr
        130             135             140

Leu Lys Tyr Val Gln Pro Asp Phe Lys Thr Ile Leu Glu Ser Pro Thr
145             150             155             160

Asp Lys Lys Val Gly Trp Lys Val Ile Phe Asn Asn Met Val Asn Gln
            165             170             175

Asn Trp Gly Pro Tyr Asp Arg Asp Ser Trp Asn Pro Val Tyr Gly Asn
            180             185             190

Gln Leu Phe Met Lys Thr Arg Asn Gly Ser Met Lys Ala Ala Asp Asn
            195             200             205

Phe Leu Asp Pro Asn Lys Ala Ser Ser Leu Leu Ser Ser Gly Phe Ser
    210             215             220

Pro Asp Phe Ala Thr Val Ile Thr Met Asp Arg Lys Ala Ser Lys Gln
225             230             235             240

Gln Thr Asn Ile Asp Val Ile Tyr Glu Arg Val Arg Asp Asp Tyr Gln
            245             250             255

Leu His Trp Thr Ser Thr Asn Trp Lys Gly Thr Asn Thr Lys Asp Lys
            260             265             270

Trp Thr Asp Arg Ser Ser Glu Arg Tyr Lys Ile Asp Trp Glu Lys Glu
            275             280             285

Glu Met Thr Asn
            290
```